(12) United States Patent
Low et al.

(10) Patent No.: US 11,623,009 B2
(45) Date of Patent: Apr. 11, 2023

(54) BONE FRACTURE REPAIR BY TARGETING OF AGENTS THAT PROMOTE BONE HEALING

(71) Applicants: Purdue Research Foundation, West Lafayette, IN (US); University of Utah, Salt Lake City, UT (US)

(72) Inventors: Stewart Andrew Low, West Lafayette, IN (US); Philip S. Low, West Lafayette, IN (US); Christopher Galliford, Silver Spring, MD (US); Jindrich Kopecek, Salt Lake City, UT (US); Jiyan Yang, Salt Lake City, UT (US)

(73) Assignees: Purdue Research Foundation, West Lafayette, IN (US); University of Utah, Salt Lake City, UT (US)

( * ) Notice: Subject to any disclaimer, the term of this patent is extended or adjusted under 35 U.S.C. 154(b) by 278 days.

(21) Appl. No.: 16/927,773

(22) Filed: Jul. 13, 2020

(65) Prior Publication Data
US 2021/0000962 A1    Jan. 7, 2021

Related U.S. Application Data

(63) Continuation of application No. 16/264,364, filed on Jan. 31, 2019, now Pat. No. 10,744,203, which is a continuation of application No. 15/578,226, filed as application No. PCT/US2016/034905 on May 29, 2016, now Pat. No. 10,279,044.

(60) Provisional application No. 62/168,421, filed on May 29, 2015.

(51) Int. Cl.
| | |
|---|---|
| *A61K 47/42* | (2017.01) |
| *A61L 27/22* | (2006.01) |
| *A61K 9/107* | (2006.01) |
| *A61K 31/404* | (2006.01) |
| *C07D 403/04* | (2006.01) |
| *C07D 209/34* | (2006.01) |
| *C07D 487/00* | (2006.01) |
| *A61L 27/54* | (2006.01) |
| *C07K 7/06* | (2006.01) |
| *C07K 7/08* | (2006.01) |
| *A61P 19/00* | (2006.01) |
| *A61M 5/00* | (2006.01) |

(52) U.S. Cl.
CPC ............ *A61K 47/42* (2013.01); *A61K 9/1075* (2013.01); *A61K 31/404* (2013.01); *A61L 27/22* (2013.01); *A61L 27/227* (2013.01); *A61L 27/54* (2013.01); *A61M 5/002* (2013.01); *A61P 19/00* (2018.01); *C07K 7/06* (2013.01); *C07K 7/08* (2013.01); *A61L 2400/06* (2013.01); *A61L 2430/02* (2013.01)

(58) Field of Classification Search
CPC .... A61K 31/404; A61K 47/42; A61K 9/1075; C07D 403/04; C07D 209/34; C07D 487/00; A61L 27/22; A61L 27/227
See application file for complete search history.

(56) References Cited

U.S. PATENT DOCUMENTS

| | | |
|---|---|---|
| 10,279,044 B2 | 5/2019 | Low et al. |
| 10,744,203 B2 | 8/2020 | Low et al. |
| 2004/0023853 A1 | 2/2004 | Peri et al. |

FOREIGN PATENT DOCUMENTS

WO    92/20371 A1    11/1992

OTHER PUBLICATIONS

International Search Report and Written Opinion issued by the ISA/US, Commissioner for Patents, dated Oct. 11, 2016, for International Application No. PCT/US2016/034905; 10 pages.
Invitation to Pay Additional Fees received for PCT Patent Application No. PCT/US2016/034905, dated Jul. 25, 2016, 2 pages.
Li, M., D. Thompson and V. Paralkar, "Prostaglandin E2 receptors in bone formation", Internal Orthopaed. (SICOT) (2007), 31: pp. 767-772. (Year: 2007).

*Primary Examiner* — Joseph R Kosack
*Assistant Examiner* — Sagar Patel
(74) *Attorney, Agent, or Firm* — Reichel Stohry Dean LLP; Natalie J. Dean; Mark C. Reichel

(57) ABSTRACT

Aspects of the present disclosure generally relate to compounds for targeting and healing bone fractures. Some of these compounds include a negatively charged oligopeptide comprising an acidic oligopeptide, a linker, which may be hydrolyzable or may be a substrate for the protease cathepsin K, and at least one molecule that promotes bone healing. In some compounds the molecule that promotes bone healing is an anabolic compound that inhibits GSK3β, in some compounds the molecule that promotes the healing of bone fracture is a pro-inflammatory agent such as PGE1. Other embodiments include methods of treating a bone fracture comprising administering a therapeutic amount of any one of the compounds disclosed herein.

13 Claims, 14 Drawing Sheets

BONE FRACTURE REPAIR BY TARGETING OF AGENTS THAT PROMOTE BONE HEALING

CROSS-REFERENCE TO RELATED APPLICATIONS

This application is a continuation application of U.S. application Ser. No. 16/264,364, filed Jan. 31, 2019, which is a continuation application of U.S. application Ser. No. 15/578,226, filed Nov. 29, 2017, (now issued as U.S. Pat. No. 10,279,044), which is a U.S. National Phase filing of PCT/US2016/034905, filed May 29, 2016, which claims the benefit of U.S. Provisional Application No. 62/168,421, filed May 29, 2015, the entire disclosures each of which is hereby expressly incorporated by reference herein in its entirety.

STATEMENT OF GOVERNMENT INTEREST

This invention was made with government support under GM069847 awarded by the National Institute of Health. The government has certain rights in the invention.

TECHNICAL FIELD

Aspects of the present disclosure generally relate to compounds for targeting and healing bone fractures, comprising a negatively charged oligopeptide, a hydrolysable linker and a bone anabolic compound and/or a pro-inflammatory agent directed toward bone growth and/or bone healing fractures and method for using the same to treat fracture of the bone.

BACKGROUND AND SUMMARY

This section introduces aspects that may help facilitate a better understanding of the disclosure. Accordingly, these statements are to be read in this light and are not to be understood as admissions about what is or is not prior art.

Healthy bone is a mix of 50-70% mineral, 20-40% organic matrix, 5-10% water, and 1-5% lipids and is constantly being recycled into new bone in order to maintain its rigidity and flexibility. (Shea, J. E. et al., Adv. Drug Deliv. Rev. 57 (2005) 945-957; Posner, A. S. and Betts, F, Acc. Chem. Res. 8 (1975) 273-281; Wang, D. et al., Bioconjug. Chem. 18 (2007) 1375-1378). At the beginning of this recycling process, monocytes receive several signals pushing them to differentiate into osteoclasts. Osteoblasts then express Receptor Activator of Nuclear Factor κ B Ligand (RANKL) to the Receptor Activator of Nuclear Factor κ B (RANK) surface receptor in monocytes, initiating the TRAF6 cascade, committing the monocytes to osteoclastogenesis. (Lacey, D. et al., Cell 93 (1998) 165-176; Yasuda, H. et al., Proc. Natl. Acad. Sci. USA 95 (1998) 3597-3602). Mature osteoclasts then initiate healthy catabolic bone resorption. Anabolic processes begin as mesenchymal stem cells (MSCs) are stimulated to become osteoblasts by the BMP-2/Runx2 and Wnt/γ-catenin pathways. Matured osteoblasts then deposit osteoid, a component of the bone matrix primarily composed of type I collagen, which mineralizes and becomes new bone. (Vaananen, H. et al., J. Cell Sci. 113 (2000) 377-381; Harada, S., Nature 423 (2003) 349-355).

A narrow balance of catabolism or anabolism is responsible for healthy bone. Alteration of this balance results in diseased bone. Osteoporosis occurs when catabolism surpasses anabolism wherein a two-standard deviation decrease in bone density from healthy bone is observed. In the US, approximately 44 million people have low bone density, and 10 million people suffer from osteoporosis. By 2020, an estimated 61 million are projected to have osteoporosis. (Bartl, R. et al., Osteoporosis: Diagnosis, prevention, therapy, Springer, 2009). In general, osteoporosis can be treated with a regimen of bisphosphonates, which inhibits osteoclasts thereby slowing catabolism as well as healthy bone turnover. This becomes problematic when bone fractures occur and proper bone turnover is retarded by bisphosphonates. These complications include crippling vertebral and hip fractures with estimated costs between in $13.7 billion and $20.3 billion in 2005. (Dempster, D. W., Am J Manag Care. 17 (2011) S164-S169).

Clinical treatment of these fractures generally does not include site-specific anabolic drugs. In fact, the only drugs approved for clinical use on fractures are BMP-2 and BMP-7, which are applied locally for use in open long bone fractures and spinal fusions. (Bishop, G. B. and Einhorn, T. A., Int. Orthop. 31 (2007) 721-727). However, the need for broader application of anabolic drugs to treat bone maladies such as osteoporotic fractures is evident when one considers that 85% of the use of anabolics are off-label. (Ong, K. L. et al., Spine 35 (2010) 1794-1800). Still, the FDA judiciously continues to limit approved use of locally administered drugs to fractures that are already open and at risk of infection.

This limitation necessitates a clinically relevant approach to treating these fractures. Therefore it would be desirable to have a fracture treatment drug that is administered systemically yet targets the fracture site.

A first embodiment of the present disclosure includes a compound for treating bone fractures, comprising: a compound of the formula X—Y—Z, wherein X is a negatively charged oligopeptide; Y is a linker; and Z is an active compound comprising at least one anabolic compound.

A second embodiment of the present disclosure includes the compound the first embodiment, wherein X is an acidic oligopeptide.

A third embodiment of the present disclosure includes the compound of the second embodiment, wherein the acidic oligopeptide comprises not less than 4 and not more than 40, or not less than 4 not less than 30, or not less than 4 and not more than 20 amino acids, or not less than 4 and not more than 15 amino acids, or not less than 4 and not more than 10 amino acids, or less than 4 and not more than 8; the number of amino acids in the oligonucleotide may be 1, 2, 3, 4, 5, 6, 7, 8, 9, 10, 11, 12, 13, 14, 15, 16 17, 18, 19, 20, or greater.

A fourth embodiment of the present disclosure includes the compound of the third embodiment, wherein the acidic oligopeptide comprises one or more amino acids selected from the group consisting of: D-aspartic acid, L-aspartic acid, D-glutamic acid, and L-glutamic acid.

A fifth embodiment of the present disclosure includes the compound of any one of the first to the forth embodiments, wherein Y is a hydrolysable linker.

A sixth embodiment of the present disclosure includes the compound of any one of the first to the fifth embodiments, wherein Y includes an oxime-ester linkage and/or the molecule 11-aminoundecanoic acid.

A seventh embodiment of the present disclosure includes the compound of any one of the first to the sixth embodiments, wherein Z is at least one anabolic compound comprising a GSK3β inhibitor.

An eighth embodiment of the present disclosure includes the compound of any one of the first to the seventh embodiments, further including at least one spacer, wherein the spacer comprises at least one molecule of 8-amino-2,6-dioxaoctanoic acid.

A ninth embodiment of the present disclosure includes the compound of any one of the first to the eighth embodiments, wherein the anabolic compound is 6'-bromoindirubin-3'-oxime.

A tenth embodiment of the present disclosure includes the compound of any one of the first to the ninth embodiments, wherein the negatively charged oligopeptides comprises D-aspartic acid.

An eleventh embodiment of the present disclosure includes the compound of any one of the first to the tenth embodiments, wherein the compound is:

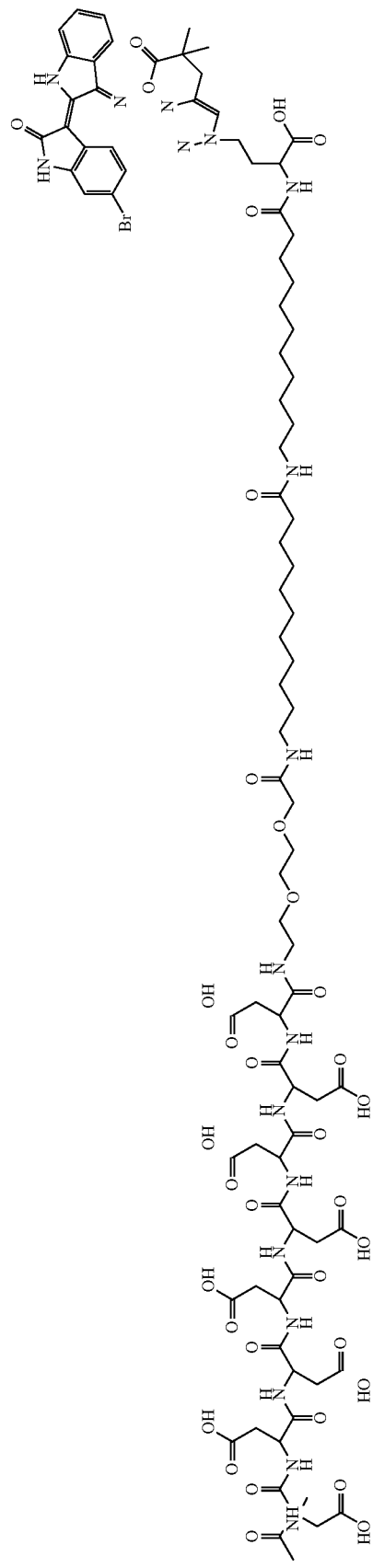

A twelfth embodiment of the compound of any one of the first to the eleventh embodiments, further comprising at least one group that can simultaneously link to Y to two or more negatively charged oligopeptides.

A thirteenth embodiment of the present disclosure includes the compound of the twelfth embodiment, comprising the following formula:

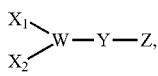

wherein:
$X_1$ and $X_2$ are either branched or linear negatively charged oligopeptides which may or may not be identical; Y is a linker; and W is at least one group comprising at least one amino acid.

A fourteenth embodiment of the present disclosure includes the compound of the thirteenth embodiment, wherein W is at least one lysine.

A fifteenth embodiment of the present disclosure includes the compound of the fourteenth embodiment, wherein the compound is:

A twenty first embodiment of the present disclosure includes the compound of any one of the sixteenth to the twentieth embodiments, wherein Y is a linker comprising at least one molecule of 11-aminoundecanoic acid.

A twenty second embodiment of the present disclosure includes the compound of any one of the sixteenth to the twenty first embodiments, wherein Z is prostaglandin E1.

A twenty third embodiment of the present disclosure includes the compound of any one of the sixteenth to the twenty second embodiments, further comprising at least one spacer, wherein the spacer comprises at least one molecule of 8-amino-2,6-dioxaoctanoic acid.

A twenty fourth embodiment of the present disclosure includes the compound of any one of the sixteenth to the twenty third embodiments, wherein the negatively charged oligopeptides comprise D-aspartic acid.

A twenty fifth embodiment of the present disclosure includes the compound of any one of the sixteenth to the twenty fourth embodiments, further comprising at least one group that can simultaneously link to Y and two or more negatively charged oligopeptides.

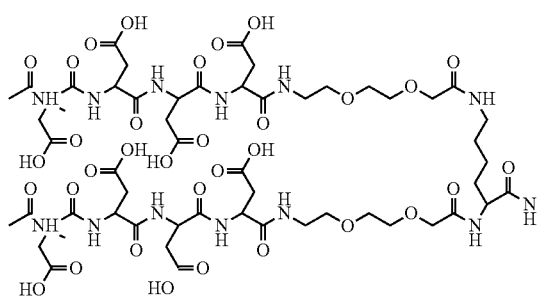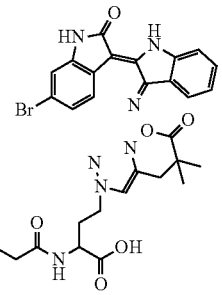

A sixteenth embodiment of the present disclosure includes a compound for treating bone fractures, comprising: a compound of the formula X—Y—Z, wherein: X is a negatively charged oligopeptide; Y is a linker; and Z is an active compound comprising at least one compound selected from the group consisting of: prostaglandin E1 and prostaglandin E2.

A seventeenth embodiment of the present disclosure includes the compound of the sixteenth embodiment, wherein X is an acidic oligopeptide.

An eighteenth embodiment of the present disclosure includes the compound of the seventeenth embodiment, wherein the acidic oligopeptide comprises not less than 4 and not more than 40, or not less than 4 not less than 30, or not less than 4 and not more than 20 amino acids, or not less than 4 and not more than 15 amino acids, or not less than 4 and not more than 10 amino acids, or less than 4 and not more than 8.

A nineteenth embodiment of the present disclosure includes the compound of the eighteenth embodiment, wherein the acidic oligopeptide comprises one or more amino acids selected from the group consisting of: D-aspartic acid, L-aspartic acid, D-glutamic acid, and L-glutamic acid.

A twentieth embodiment of the present disclosure includes the compound of any one of the sixteenth to the nineteenth embodiments, wherein Y is a hydrolysable linker.

A twenty sixth embodiment of the present disclosure includes the compound of the twenty fifth embodiment, comprising the following formula:

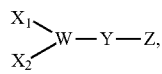

wherein:
$X_1$ and $X_2$ are either branched or linear negatively charged oligopeptides which may or may not be identical to one another; Y is a linker; and W is at least one group comprising at least one amino acid.

A twenty seventh embodiment of the present disclosure includes the compound of the twenty sixth embodiment, wherein W is at least one lysine.

A twenty eighth embodiment of the present disclosure includes a method of treating a bone fracture, comprising the steps of: administering a therapeutic amount of any one of the compounds to a patient suffering from the bone fracture.

A twenty ninth embodiment of the present disclosure includes the method of the twenty eighth embodiment, further comprising the step of: identifying a patient having a bone fracture.

A thirtieth embodiment of the present disclosure includes a method of treating a bone fracture, comprising the step of: administering to a patient suffering from the bone fracture a therapeutic amount of a compound of the formula, A-B-(MA)$_n$-C-D wherein:

A is at least one negatively charged oligopeptide; B is a spacer; C is a linker, wherein the linker includes at least one oligopeptide that is a substrate for the protease cathepsin K; D is an active compound that promotes the healing of bone fractures comprising at least one compound selected from the group consisting of: prostaglandin E1 and prostaglandin E2; MA is a backbone structure which is linked to both B and C; and n is 1 to 20, or 1 to 100, or 1 to 200, or 1 to 300, or 1 to 400, or 1 to 500, or 1 to 600, or 1 to 700, or 1 to 800, or 1 to 900, or 1 to 1,000, 1 to 1500, 1 to 2000, or any digit greater than or equal to 1 and less than or equal to 2,000; n may 1, 2, 3, 4, 5, 6, 7, 7, 8, 9, 10, 11, 12, 13, 14, 15, 16, 17, 18, 19, 20, or an digit in the series up to and including 1000.

A thirty first embodiment of the present disclosure includes the method of the thirtieth embodiment, further comprising the step of: identifying a patient having a bone fracture.

A thirty second embodiment of the present disclosure includes the method of any one of the thirtieth to the thirty first embodiments, wherein A is an acidic oligopeptide.

A thirty third embodiment of the present disclosure includes the method of any one of the thirtieth to the thirty third embodiments, wherein the acidic oligopeptide comprises not less than 4 and not more than 40, or not less than 4 not less than 30, or not less than 4 and not more than 20 amino acids, or not less than 4 and not more than 15 amino acids, or not less than 4 and not more than 10 amino acids, or less than 4 and not more than 8.

A thirty fourth embodiment of the present disclosure includes the method of any one of the thirtieth to the thirty third embodiments, wherein the acidic oligopeptide comprises one or more amino acids selected from the group consisting of: D-aspartic acid, L-aspartic acid, D-glutamic acid, and L-glutamic acid.

A thirty fifth embodiment of the present disclosure includes the method of any one of the thirtieth to the thirty fourth embodiments, wherein B is a spacer comprising at least one glycine and at least one 8-amino-2,6-dioxaoctanoic acid.

A thirty sixth embodiment of the present disclosure includes the method of any one of the thirtieth to the thirty fifth embodiments, wherein C comprises at least one glycine.

A thirty seventh embodiment of the present disclosure includes the method of any one of the thirtieth to the thirty sixth embodiments, wherein C is a linker having the formula:

-Gly-Gly-Pro-Xle-, wherein:

Gly is a glycine; Pro is a proline; and Xle comprises at least one moiety selected from the group consisting of: norleucine, leucine, isoleucine, a hydrophobic amino acid, and an amphipathic amino acid.

A thirty eighth embodiment of the present disclosure includes the method of any one of the thirtieth to the thirty seventh embodiments, wherein D is prostaglandin E1.

A thirty ninth embodiment of the present disclosure includes the method of any one of the thirtieth to the thirty eighth embodiments, wherein MA comprises at least one N-(2-Hydroxypropyl) methacrylamide.

A fortieth embodiment of the present disclosure includes the method of any one of the thirtieth to the thirty ninth embodiments, wherein the compound of the formula A-B-(MA)$_n$-C-D is:

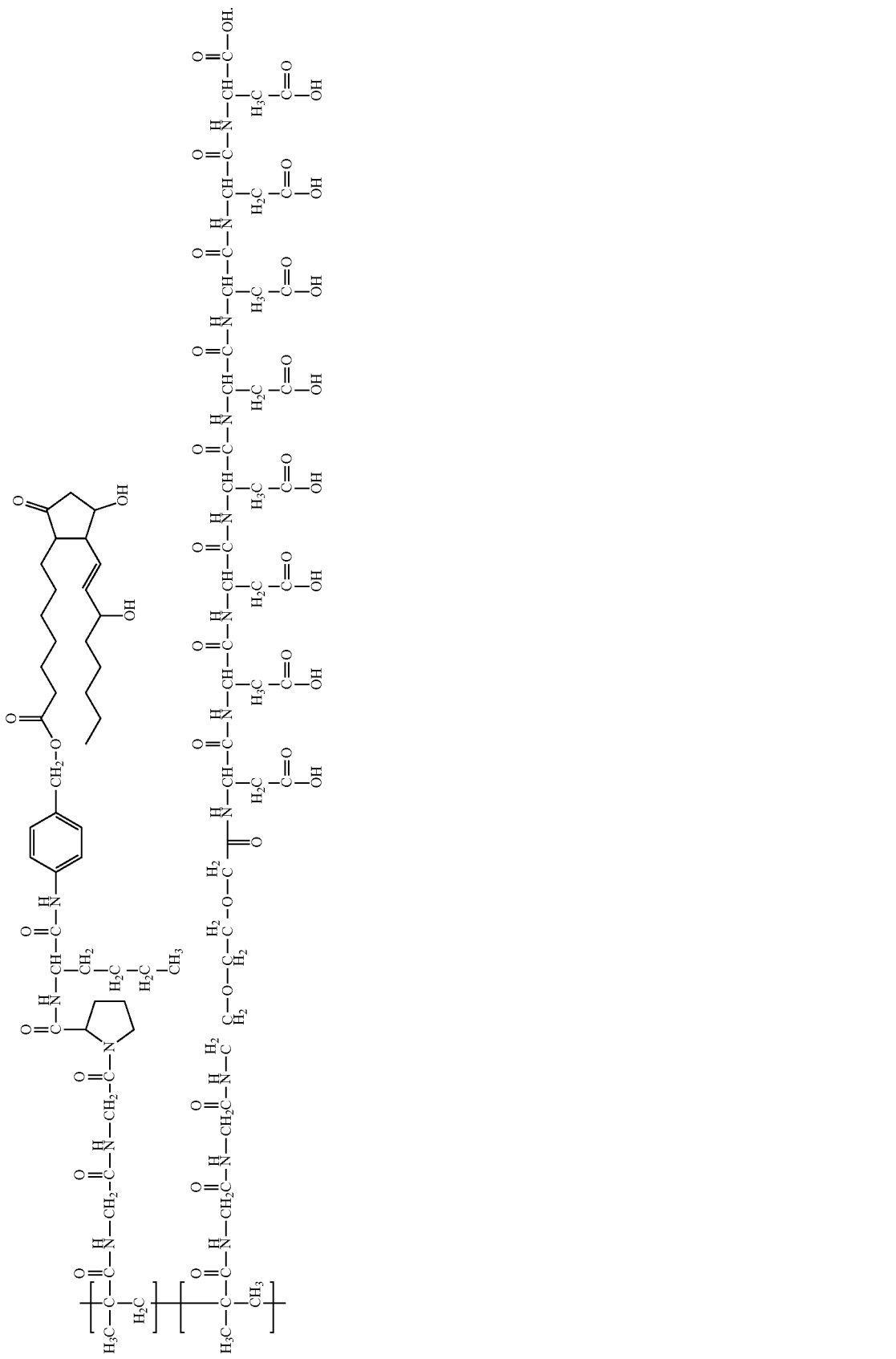

A forty first embodiment of the present disclosure includes the method of any one of the thirtieth to the fortieth embodiments, wherein the compound of the formula: A-B-(MA)$_n$-C-D, further comprises at least one molecule of 2-(6-hydroxy-3-oxo-3H-xanthen-9-yl)-5-(3-(3-methacrylamidopropyl)thioureido)benzoic acid, wherein the at least one molecule of 2-(6-hydroxy-3-oxo-3H-xanthen-9-yl)-5-(3-(3-methacrylamidopropyl)thioureido)benzoic acid is linked to MA.

A forty second embodiment of the present disclosure includes the method of any one of the thirtieth to the forty first embodiments, wherein the compound of the formula A-B-(MA)$_n$-C-D further comprises a third group that linked to (MA)$_n$, and/or a fourth group that linked to (MA)$_n$, and/or a fifth group that linked to (MA)$_n$. Some embodiments includes the method of any one of the thirtieth to the forty first embodiments, wherein 1 to 20, or 1 to 100, or 1 to 200, or 1 to 300, or 1 to 400, or 1 to 500, or 1 to 600, or 1 to 700, or 1 to 800, or 1 to 900, or 1 to 1,000, 1 to 1500, 1 to 2000, or any digit greater than or equal to 1 and less than or equal to 2,000 groups, which may or may not be identical to one another, are linked to (MA)$_n$.

A forty third embodiment of the present disclosure includes the method of the forty second embodiment, wherein the compound has the following formula:

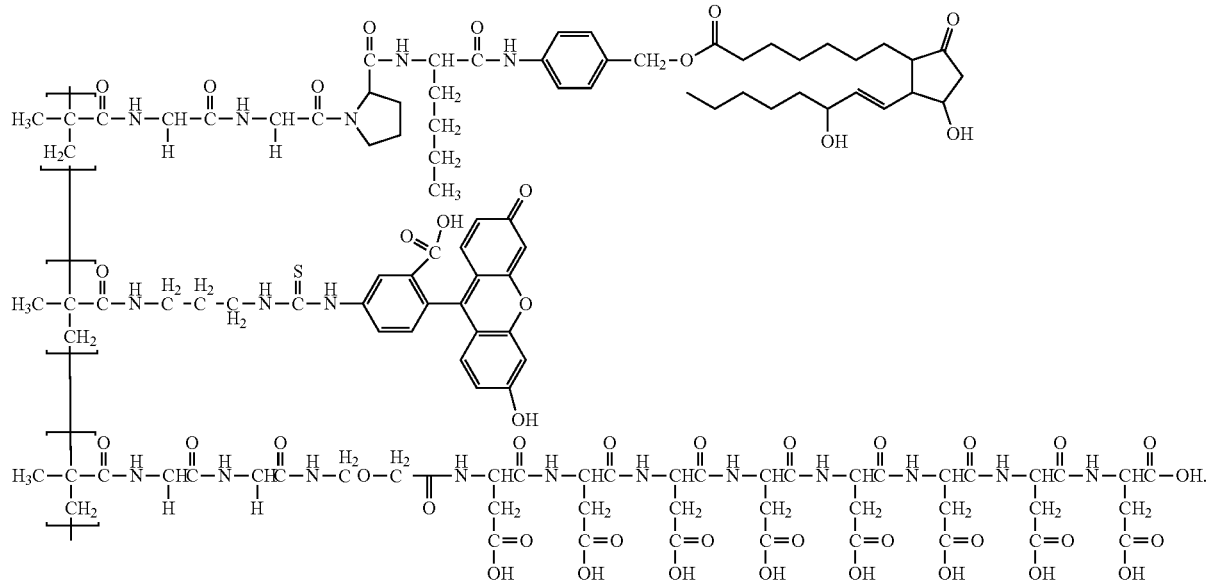

A forty fourth embodiment of the present disclosure includes the method of any one of the thirtieth to the forty second embodiments, wherein the negatively charged oligopeptides comprise D-aspartic acid.

A forty fifth embodiment of the present disclosure includes a method of treating a bone fracture, comprising the step of: administering to a patient suffering from the bone fracture a therapeutic amount of a compound of the formula, A-B-(MA)$_n$-C-D, wherein:

A is a negatively charged oligopeptide; B is a spacer; C is a linker, wherein the linker includes at least one oligopeptide that is a substrate for the protease cathepsin K; D is an active compound comprising at least one anabolic compound; MA is a backbone structure which is linked to both B and C; and n is 1 to 20, or 1 to 100, or 1 to 200, or 1 to 300, or 1 to 400, or 1 to 500, or 1 to 600, or 1 to 700, or 1 to 800, or 1 to 900, or 1 to 1,000, 1 to 1500, 1 to 2000, or any digit greater than or equal to 1 and less than or equal to 2,000; n may be 1, 2, 3, 4 5, 6, 7, 8, 9, 10, 11, 12, 13, 14, 15, 16, 17, 18, 19, 20, or any greater number up to and including 1000.

A forty sixth embodiment of the present disclosure includes the method of the forty fifth embodiment, further comprising the step of: identifying a patient having a bone fracture.

A forty seventh embodiment of the present disclosure includes the method of any one of the forty fifth to the forty sixth embodiments, wherein A is an acidic oligopeptide.

A forty eighth embodiment of the present disclosure includes the method of any one of the forty fifth to the forty seventh, wherein the acidic oligopeptide comprises not less than 4 and not more than 40, or not less than 4 not less than 30, or not less than 4 and not more than 20 amino acids, or not less than 4 and not more than 15 amino acids, or not less than 4 and not more than 10 amino acids, or less than 4 and not more than 8; the number of amino acids in the oligopeptide may be 1, 2, 3, 4, 5, 6, 7, 8, 9, 10, 11, 12, 13, 14, 15, 16, 17, 18, 19, 20, or more.

A forty ninth embodiment of the present disclosure includes the method of any one of the forty fifth to the forty eighth embodiments, wherein the acidic oligopeptide comprises one or more amino acids selected from the group consisting of: D-aspartic acid, L-aspartic acid, D-glutamic acid, and L-glutamic acid.

A fiftieth embodiment of the present disclosure includes the method of any one of the forty fifth to the forty ninth embodiments, wherein B is a spacer comprising at least one glycine and at least one 8-amino-2,6-dioxaoctanoic acid.

A fifty first embodiment of the present disclosure includes the method of any one of the forty fifth to the fiftieth embodiments, wherein C comprises at least one glycine.

A fifty second embodiment of the present disclosure includes the method of any one of the forty fifth to the fifty first embodiments, wherein C is a linker having the formula:

-Gly-Gly-Pro-Xle-, wherein:

Gly is a glycine; Pro is a proline; Xle comprises at least one moiety selected from the group consisting of: norleucine, leucine, isoleucine, a hydrophobic amino acid, and an amphipathic amino acid.

A fifty third embodiment of the present disclosure includes the method of any one of the forty fifth to the fifty second embodiments, wherein D is at least one anabolic compound comprising a GSK3β inhibitor.

A fifty fourth embodiment of the present disclosure includes the method of any one of the forty fifth to the fifty third embodiments, wherein the anabolic compound is 6'-bromoindirubin-3'-oxime.

A fifty fifth embodiment of the present disclosure includes the method of any one of the forty fifth to the fifty fourth embodiments, wherein MA comprises at least one N-(2-Hydroxypropyl) methacrylamide.

A fifty sixth embodiment of the present disclosure includes the method of any one of the forty fifth to the fifty fifth embodiments, wherein the negatively charged oligopeptides comprise D-aspartic acid.

A fifty seventh embodiment of the present disclosure includes a kit for treating a bone fracture comprising: at least one therapeutically effective dose of any of the compound of to any one of the first to the fifty sixth embodiments, or a pharmaceutically acceptable salt thereof.

A fifty eighth embodiment of the present disclosure includes the kit of to the fifty seventh embodiment, wherein said compound in the kit is formulated for injection.

A fifty ninth embodiment of the present disclosure includes the kit of to the fifty eighth embodiment, wherein said compound in the kit is formulated with at least one additional material that helps to preserve the activity of said compound.

A sixtieth embodiment of the present disclosure includes a compound having the formula: Acidic oligopeptide-linker-inhibitor, wherein the acidic oligopeptide comprises from 6 to about 10 aspartic acid units, the linker is a hydrolysable linker comprising (11-aminoundecanoic acid)$_2$ and the inhibitor is a GSK3β inhibitor.

A sixty first embodiment of the present disclosure includes the compound of the sixtieth embodiment, wherein the GSK3β inhibitor is 6'-bromoindirubin.

A sixty second embodiment of the present disclosure includes the compound of the sixtieth embodiment, wherein the compound is:

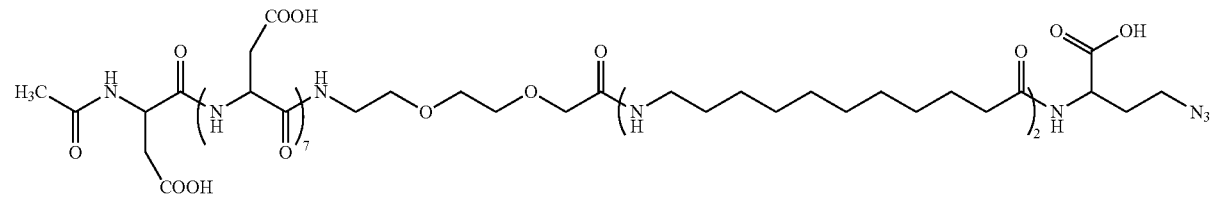

A sixty third embodiment of the present disclosure includes the compound of sixtieth embodiment, wherein the compound is:

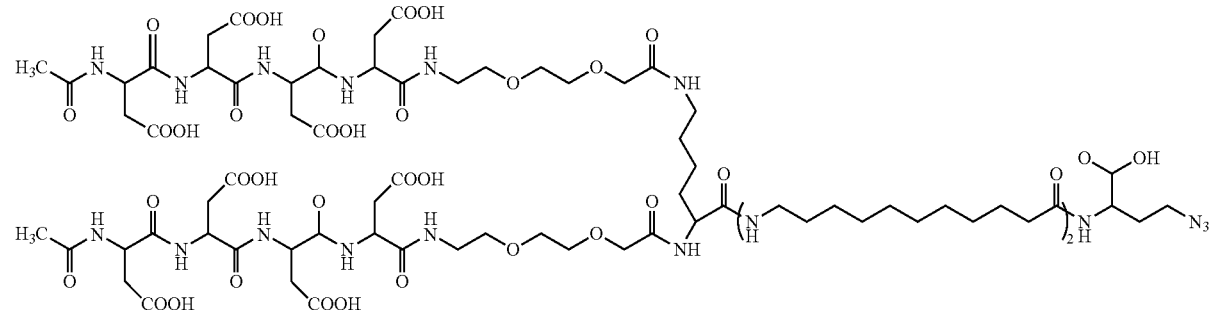

A sixty fourth embodiment of the present disclosure includes a micelle comprising any of the compounds of the sixtieth to the sixty third embodiments.

A sixty fifth embodiment of the present disclosure includes a method of treating a bone fracture comprising administering a therapeutic amount of any of the compounds of the sixtieth to the sixty fourth embodiments.

A sixty fifth embodiment of the present disclosure includes the compound of any of the sixtieth to the sixty fourth embodiments, wherein the aspartic acid units comprise D-aspartic acid.

DETAILED DESCRIPTION

Figure 1:
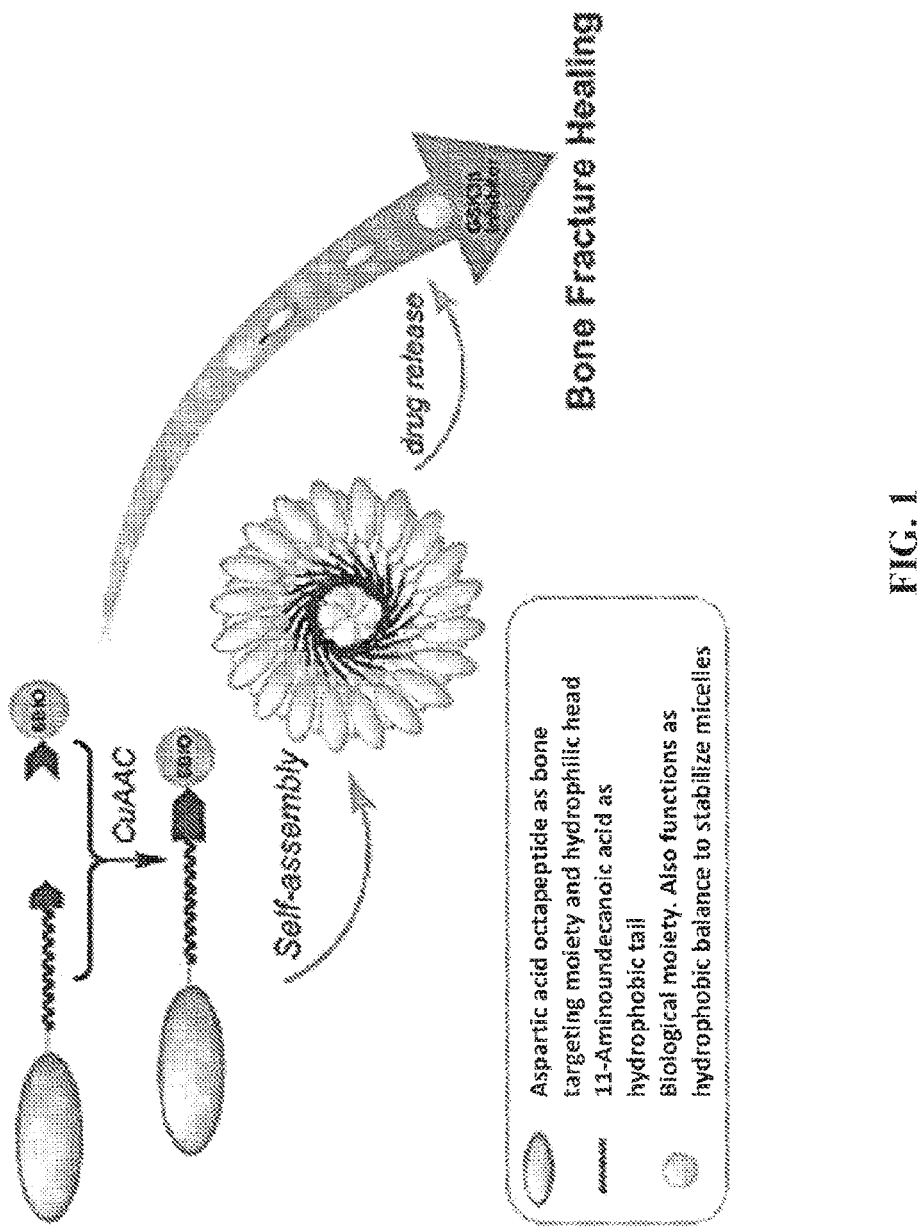
FIG. 1. A schematic cartoon illustrating a fracture-targeting micelle of the present invention.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

Some aspects of the present invention provide compounds for targeting and healing bone fractures, wherein the compound may comprise three structural/functional regions: a negatively charged oligopeptide, a hydrolysable linker and a compound that exhibits bone anabolic behavior which promotes bone growth and/or the healing of fracture of the bone. In some embodiment the negatively charged oligopeptide may be comprised of one or more D or L aspartic acid residues; the negatively changed oligopeptide is thought to help direct the compound to the bone fracture site. The hydrolysable linker provides a means of attaching the compound that promotes bone healing to the compound the presence of the hydrolyzable group allows the compound possessed of bone healing activity to be detached from the compound; in some aspects at least one portion of the bone healing compound is release at or near the bone fracture site. In some aspects the portion of the compound of the present invention that accelerates healing of the bone a molecule that exhibits the anabolic activity; in some embodiment this molecule may act and an inhibitor of GSK3β activity. Some non-limiting examples of such compounds of the present invention may be found in FIGS. 1 and 2.

With an aging population and an increase in prescription bisphosphonates, debilitating non-union and delayed union bone fractures are inevitable. The development of a bone anabolic agent delivery system has not caught up with the demand of an aging population. With an aging population and an increase in prescription bisphosphonates, debilitating non-union and delayed union bone fractures are inevitable. The development of a bone anabolic agent delivery system has not caught up with the demand of an aging population. Current practice is directed toward applying anabolic compounds directly to the fracture. This entails exposing the bone, increasing healing time, pain and discomfort and the possibility of infection. In contrast the compound of the present invention may be given systemically, either orally or intravenously, and migrates preferentially to the fracture site. See Low S. A. et al., *Biodistribution of Fracture-Targeted GSK3β Inhibitor-Loaded Micelles for Improved Fracture Healing*, BIOMACROMOLECULES. 2015 Oct. 12; 16(10):3145-53, disclosure of which is incorporated by reference in its entirety to the extent they are not inconsistent with the explicit teachings of this specification.

In one aspect of the present invention, the compound comprises an acidic oligopeptide comprising a plurality of aspartic acid residues. The number of D or L aspartic acid residues may be from about 4 to about 10 residues. The oligopeptide may be linear or it may be branched. In one illustrative embodiment, a lysine residue is used as the branch point. In another aspect of the present invention, the aspartic acid may be either L-aspartic acid, D-aspartic acid or a mixture of either enantiomer. An advantage of including the D-aspartic acid in the oligopeptide is that it may be less susceptible to proteolytic degradation as compared to an oligopeptide comprising only the naturally-occurring L-aspartic acid.

In another aspect of the present invention, the compound may comprise a bone anabolic compound such as a GSK3β inhibitor. The inhibition of GSK3β has been shown to result in growth of new bone and bone fracture healing. Examples of GSK3β inhibitors include, but are not limited to, lithium chloride and 6-bromoindirubin-3'-oxime (6BIO).

In another aspect, the present invention provides a hydrolysable linker for joining the acidic oligopeptide to the bone anabolic compound. The hydrolysable linker may comprise a hydrophobic region and a cleavable oxime moiety closest to the anabolic compound. The oxime moiety is cleavable under basic conditions or neutral conditions (pH 6.9-7.4) such as that found at a bone fracture site. The hydrophobic region may comprise two molecules of 11-aminoundecanoic acid joined together.

In a further aspect, the present invention provides a micelle comprising a multiplicity of the compound of the present invention. The compound, classified here as a unimer, comprises a hydrophilic end in the acidic oligopeptide and a hydrophobic end with the 6BIO. The hydrophobic linker further stabilizes the hydrophobic end of the micelle. The use of a micelle for systemic treatment of fractures may be advantageous due to the stability of micelle and the concentrated amount of anabolic compound that can be delivered to the fracture site. The invention will be further clarified by various following non-limiting examples.

Example 1. Biodistribution of Fracture-Targeted GSK3β-Loaded Micelles for Improved Fracture Healing Experimental Procedures Materials: Solvents, dimethylformamide (DMF), dichloromethane (DCM), methanol (MeOH), dimethyl sulfoxide (DMSO), ethyl acetate, ether, and acetonitrile (ACN) were purchased from VWR, Fisher Scientific, or Sigma-Aldrich and were reagent grade or better. Piperidine, diisopropyl ethylamine (DIPEA), trifluoroacetic acid (TFA), triisoproyl silane (TIS), ethylenebis(diphenylphosphine) (DPPE), lithium hydroxide, bis(benzonitrile)palladium(II) chloride, copper(I) bromide, Chloramine T trihydrate, lithium diisopropyl amide (LDA), propargyl chloride, and sodium carbonate (Na2CO3), were purchased from Sigma-Aldrich. Sodium sulfate was purchased Macron Chemicals. Fmoc-11-aminoundecanoic acid (Fmoc-AUA), 1-[bis(dimethylamino)methylene]-1H-1,2,3-triazolo[4,5-b]-pyridinium 3-oxide hexafluorophosphate (HATU), chloro-trityl resin, and N-9-fuorenylmethoxycarbonyl-L-aspartic acid (Fmoc-L-Asp-OH) were purchased from AKsci. N-2-N-6-Bis(9-fluorenyl-methyloxycarbonyl)-L-lysine (Fmoc-Lys(Fmoc)-OH) was purchased from Aapptec and 9-fluorenylmethoxycarbonyl-8-amino-3,6-dioxaoctanoic acid (Fmoc-miniPEG) was purchased from BioBlocks. Sephadex LH20 beads were purchased from Amersham Pharmacia Biotech AM. Fmoc-Azidohomoalanine (Fmoc-Dab (N3)-OH), 3-acetoxylindole, and Bromostatin were purchased from Chem-Impex International.

Synthesis of 6'-bromoindirubin (I). 6'-Bromoindirubin was synthesized as previously described in the literature with modifications [Polychronopoulos, P.; Magiatis, P.; Skaltsounis, A.-L.; Myrianthopoulos, V.; Mikros, E.; Tarricone, A.; Musacchio, A.; Roe, S. M.; Pearl, L.; Leost, M.; Greengard, P.; Meijer, L. J. Med. Chem. 2004, 47 (4), 935-946.]. Briefly, 615 mL of anhydrous methanol was set stirring under nitrogen in a 2 L round bottom flask. 6-Bromoisatin 3.37 g (15 mmol) and 3-acetoxylindole 2.63 g (15 mmol) were then added and the solution was bubbled with nitrogen for 45 min. Anhydrous sodium carbonate 3.98 g (37.5 mmol) was added and the reaction was stirred for 5 h in the dark. The resultant dark purple precipitate was isolated by centrifugation, the solid decanted with methanol and re-suspended in ethyl acetate. The 6'-bromoindirubin was washed 3× with brine. The organic layer was dried with sodium sulfate and the solvent removed under reduced pressure to yield a dark purple solid. Yield: >90%, mass: 338.94, 340.93 (the two masses are due to the two common isotopes of bromine).

Synthesis of 6'-bromoindirubin-3'-oxime (II, 6BIO). 6'-bromoindirubin-3'-oxime (6BIO) was synthesized as described in Polychronopoulos et al. (J. Med. Chem. 47 (2004) 935-946). 6-Bromoindirubin 3.06 g (9 mmol) and hydroxylamine hydrochloride 6.25 g (90 mmol) were combined in a pressure reaction tube. Ninety mL of pyridine was added and purged under argon for 30 min. The reaction was sealed and stirred at 115-120° C. for 2.5 h. The pyridine was removed under reduced pressure and the dark red product solid was washed with hexanes. The product was suspended in ethyl acetate and washed 2× with water followed by a wash with brine. The organic phase was dried with sodium sulfate and solvent removed under reduced pressure yielding a dark red solid. Yield>90% mass: 353.96, 355.96. The compound 6BIO was purified to baseline resolution using HPLC, and its structure was confirmed by Mass Spectrometry (data not shown, and NMR. Representative NMR assignments for the compound are as follows: $^1$H NMR (500 MHz, DMSO-$d_6$) δ 11.74 (s, 1H), 10.84 (s, 1H), 8.54 (d, J=8.5 Hz, 1H), 8.21 (dd, J=7.6, 1.0 Hz, 1H), 7.44-7.39 (m, 2H), 7.08 (dd, J=8.4, 2.0 Hz, 1H), 7.06-7.02 (m, 1H), 7.01 (d, J=2.0 Hz, 1H).

Synthesis of 2,2-dimethylpent-4-ynoic acid. Briefly, a round bottom flask was dried and purged with nitrogen and cooled to −78° C. LDA 2M 6.1 mL (13 mmol) was added and a stream of nitrogen was used to bubble the reaction. Methyl isobutyrate 1.6 mL (14 mmol) was added dropwise as the reaction was stirred. Propargyl chloride 891 μL (10 mmol) was also added dropwise as the reaction was stirred vigorously. The solution was allowed to warm to room temperature and was stirred overnight. The reaction was then quenched with concentrated NH4Cl and extracted with ethyl acetate. The organic layer was dried with sodium sulfate and solvent removed under reduced pressure until a yellow oil remained.

Lithium hydroxide 480 mg (20 mmol) and MeOH were added to the product and stirred overnight, removing the methyl ester. Water was added to the reaction and acidified to pH 2 prior to extracting twice with ethyl acetate. The organic layer was dried with sodium sulfate and the solvent was removed under reduced pressure. Yield was 7% (2,2-dimethylpent-4-ynoic acid).

Synthesis of (2Z,3E)-6'-bromo-3-(((2,2-dimethylpent-4-ynoyl)oxy)imino)-[2,3'-biindolinylidene]-2'-one (III). Briefly, 6BIO was conjugated to 2,2-dimethylpent-4-ynoic acid using standard DCCassisted ester coupling. 6BIO 18 mg (0.05 mmol), 2,2-dimethylpent-4-ynoic acid (7.5 mg; 0.06 mmol), and DCC 12.4 mg (0.06 mmol) were added to 3 mL of DMF under nitrogen. DIPEA 26 μL (0.15 mmol) was then added and the reaction was stirred under nitrogen for 4 h. The product was filtered and dissolved in ethyl acetate. The solution was then washed 3 times with water and dried with sodium sulfate. The solvent was removed under reduced pressure onto celite (diatomite) and purified using flash chromatography (hexanes/ethyl acetate) Yield: 80% (data not shown).

The compound 6BIO and 2,2-dimethyl-3-butynoic acid was purified to baseline resolution using HPLC, and its structure was confirmed by Mass Spectrometry (data not shown, and NMR. Representative NMR assignments for the compound are as follows: $^1$H NMR (500 MHz, DMSO-$d_6$) δ 11.62 (s, 1H), 11.00 (s, 1H), 9.06 (d, J=8.5 Hz, 1H), 8.28-8.05 (m, 1H), 7.53 (ddd, J=8.3, 7.2, 1.2 Hz, 1H), 7.49 (dt, J=8.0, 1.0 Hz, 1H), 7.14 (td, J=7.5, 1.2 Hz, 1H), 7.11 (dd, J=8.5, 2.0 Hz, 1H), 7.03 (d, J=1.9 Hz, 1H), 2.97 (t, J=2.6 Hz, 1H), 2.69 (d, J=2.7 Hz, 2H), 1.47 (s, 6H).

Synthesis of amphiphilic unimers flanked with C-terminal azide. Unimers were synthesized as previously described with slight modifications. (Low, S. A. et al., Bioconjug. Chem. 25 (2014) 2012-2020.) Briefly, in a small glass vial, 2-chlorotrityl resin (1.11 mmol/g) was loaded at 0.4 mmol/g with Fmoc-Dab(N3)-OH overnight in DCM and DIPEA. The resin was transferred to a SPPS vessel capable of bubbling nitrogen. The resin was then capped with four 5 mL washes of DCM: MeOH:DIPEA (17:2:1) followed by three washes of DMF. Following each amino acid addition, Fmoc-groups were removed during two 20-min incubations with 20% (v/v) piperidine in DMF. The resin was then washed three times with DMF prior to the next amino acid being added. Fmoc-AUA was added twice in a five-fold excess using HATU/DIPEA. Following addition of Fmoc-AUA, branched unimers (N3-A2-K-D4) were prepared by adding Fmoc-Lys(Fmoc)-OH followed by miniPEG and 4 aspartic acids. Linear unimers were created by adding miniPEG and 8 aspartic acids to the AUA. Both unimers were capped with acetic acid, HATU, and DIPEA. The final resin-bound products were washed with DMF, DCM, MeOH (3× each) and dried under nitrogen. The products were cleaved from resin using TFA: TIS: H2O (90:5:5) and precipitated in diethyl ether prior to HPLC purification.

Click conjugation of (2Z, 3E)-6'-bromo-3-(((2,2-dimethylpent-4-ynoyl)oxy)imino)-[2,3'-biindolinylidene]-2'-one to unimers. N3-A2-D8 and N3-A2-K-D4 (both 0.01 mmol) were dissolved in DMF and purged with nitrogen for 20 min. Additional DMF was purged with nitrogen and was used to dissolve a mixture of (2Z,3E)-6'-bromo-3-(((2,2-dimethylpent-4-ynoyl)oxy)imino)-[2,3'-biindolinylidene]-2'-one (0.03 mmol), copper(I)bromide (0.01 mmol), and TBTA (0.01 mmol). The two solutions were combined and stirred under nitrogen for 20 min. Ascorbic acid (0.01 mmol) and a drop of water were then added. The reaction proceeded for 40 min after which it was diluted in MeOH and purified on LH20 column. The fractionated peaks were dried under reduced pressure. Yields for BIO-A2-D8 and BIO-A2-K-D8 were 65% and 48%, respectively.

The structures of unimers (e.g., A2-D8, A2-K-D4, BIO-A2-D8, and BIO-A2-K-D4) were confirmed using HPLC, Mass Spectrometry, and NMR (data not shown).

Dynamic light scattering measurements of micelles. The hydrodynamic radius of the micelles were determined using Malvern Zetasizer Nano ZS. Measurements of both unimers were taken using 2.4 nmol/mL unimer at 25° C. Malvern software was used to determine hydrodynamic diameter.

Release kinetics of 6BIO from micelles. Release kinetics were measured for each of the micelles. Unimer (0.1 mg) was dissolved in 1 mL of PBS containing 30% MeOH. Samples for each time point (0, 1 h, 2 h, 4 h, 8 h, 12 h, and 24 h) were made in triplicate. Each sample was incubated in a water bath at 37° C. for the allotted length of time. Each sample was then measured at λ=290 nm on an Agilent 1200 (0.01 M NH4HCO3, ACN). Area under the curve was measured using MestReNova software and the percent of the drug peak released was calculated as follows:

$$\frac{\text{Free } 6BIO}{\text{Free } 6BIO + \text{Micellar } 6BIO} \times 100$$

Stannylation of 6BIO. Stannylation of 6BIO was performed as previously described for other indols. (Corcoran, E. B. et al., Org. Lett. 14 (2012) 4630-4633.) To a pressure tube, 6BIO (1 mmol) was dissolved in 20 mL dioxane and purged with argon for 30 min. PdCl2(PhCN)2 (0.05 mmol), DPPE (0.1 mmol), and tributyl tin (3 mmol) were then added. The tube was purged with argon for an additional 10 min and sealed. The reaction was stirred vigorously at 110° C. for 12 h. The product was dried on celite and purified using flash chromatography (hexanes 1% TEA/EtOAc). The solvent was removed under reduced pressure resulting in a brown red solid (2Z,3E)-3-(hydroxyimino)-6'-(tributylstannyl)-[2,3'-biindolinylidene]-2'-one.

O-Alkylation of stannylated BIO ((2Z,3E)-3-(hydroxyimino)-6'-(tributylstannyl)-[2,3'-biindolinylidene]-2'-one). DMF was added to a mixture of (2Z,3E)-3-(hydroxyimino)-6'-(tributylstannyl)-[2,3'-biindolinylidene]-2'-one (56 mg; 0.1 mmol), propargyl chloride (7.2 µL; 0.1 mmol), and cesium carbonate 38 mg (0.1 mmol) and stirred vigorously. The reaction was monitored every half hour throughout the reaction by LC/MS. At 1.5 h a small amount of dialkylated side-product was formed, and the reaction was stopped by adding water. The product was then extracted into EtOAc and washed 3 times with water and dried on sodium sulfate. Celite was added and the solvent was removed by reduced pressure. The product was purified by reverse phase chromatography (H2O-1% DIPEA; ACN-1% DIPEA). The product, (2Z,3E)-3-((prop-2-yn-1-yloxy)imino)-6'-(tributylstannyl)-[2,3'-biindolinylidene]-2'-one, was brownish purple.

Conjugation of alkylated stannylated 6BIO to unimers. Each unimer (N3-A2-D8 or N3-A2-K-D4) (0.01 mmol) was dissolved in DMF and purged with nitrogen for 20 min. To a separate vial of DMF purged with nitrogen (2Z,3E)-3-((prop-2-yn-1-yloxy)imino)-6'-(tributylstannyl)-[2,3'-biindolinylidene]-2'-one (0.03 mmol), copper(I)bromide (0.01 mmol), DIPEA (0.1 mmol), and TBTA (0.01 mmol) were added. The two solutions were combined and stirred under nitrogen for 40 min. Upon completion the reaction was diluted in MeOH and purified on LH20 column (MeOH 1% DIPEA). The fractionated peaks were dried under reduced pressure yielding a bluish purple solid.

Radio-iodination of micelles and 6BIO. The stannylated unimers and stannylated 6BIO (0.3-0.5 µmol) were dissolved in 100 µL DMF. The solutions were transferred to Wheaton V-vials containing a solution of [$^{125}$I]NaI (5.0 mCi) in 100 µL DMF phosphate-buffered saline (PBS) (pH 7.4). Chloramine-T was added, and the reaction mixture stirred for 15 min at ambient temperature. Purification of the iodinated micelles was performed using a LH20 column eluted with MeOH. Iodinated 6BIO was dissolved in EtOAc and was washed twice with water. The solvent of all three reactions was evaporated using a stream of nitrogen, and the residue was dissolved with PBS (pH 7.4) to obtain solutions with an activity concentration of 370 kBq/100 µL. The overall radiochemical yield was ca. 10%.

Murine fracture induction. All animal studies were done in accordance to Purdue's animal care and use committee protocol and were done performed as described in the literature. CD4 Swiss mice (30-35 g) acquired from Harlan laboratories were used for these experiments. A stabilized femoral fracture was performed under aseptic conditions with isoflurane anesthesia. Skin around the knee was shaved and cleaned with an alcohol pad first, then with Betadine solution. The skin incision was made medial parapetellar. The patella was then dislocated and an incision was made under the patella. A 25 gauge needle was used to ream the intramedullary canal. A 22 guage locking nail (where both ends are flattened to produce rotational stability), was then inserted. The wound was sutured and the bone was then fractured using a three point bending device that has a built-in stop to prevent excess injury. Subcutaneous Buprenorphine (0.05-0.1 mg/kg) was administered at the time of surgery, followed by a dose every 12 h for 3-7 days post operation.

Injection and dissection techniques/counting for 24 h biodistribution. From the iodinated products described previously 1 uCi/mL solutions were made in sterile PBS. The study was performed on 3 groups of mice with 5 mice per group. Two weeks following fracture induction, each mouse received a 0.1 µCi (0.1 mL) dose of the radio-iodinated linear micelles, branched micelle, or free drug. Animals were then placed back in their cages for 24 h. At 24 h they were sacrificed using CO2 excess. Blood was drawn from a cardiopuncture and all other organs measured were removed (lungs, liver, spleen, kidneys, fractured femur, healthy femur). The activity was counted using Packard Cobra Auto-Gamma and was normalized by dividing the count rate by the weights of each organ.

Injection and imaging techniques for imaging. From the iodinated products described previously, 1 mCi/mL solutions were made in sterile PBS. The study was performed on 3 groups of mice with 5 mice per group. Two weeks following fracture induction each mouse received 0.1 mCi (0.1 mL) of dose. Animals were then returned to their cages until euthanasia by $CO_2$ overdose at the desired time point (1 h, 4 h, 24 h). Animals were imaged using MiLabs U-SPECT-II/CT. 3D reconstructions were performed using Image J software.

Results and Discussion

Design and characterization of micelles. One of the goals of the work disclosed herein was to develop a fracture-targeted anabolic-loaded micelle capable of utilizing the unique microenvironment available in bone fractures. That is, freshly exposed hydroxyapatite (HAp) due to a fracture, additional HAp exposed by osteoclasts during resorption, newly exposed calcified bone, and the local inflammatory response.

HAp can be targeted using any one of several bone adsorbing ligands including bisphosphonates, tetracycline, and acidic oligopeptides. Both bisphosphonates and tetracycline have biocompatibility issues with osteonecrosis of the jaw and the staining teeth yellow, respectively. (Marx, R. E. et al., J. Oral Maxillofac. Surg. 63 (2005) 1567-1575; Hoff, A. O. et al., J. Bone Miner. Res. 23 (2008) 826-836; Madison, J. F., Arch. Dermatol. 88 (1963) 58-59). In order to maintain bone homeostasis, the more biocompatible option is acidic oligopeptides. Aspartic acid octapeptide, as evidence suggests, is near an ideal number of aspartic acids to ensure rapid binding (data not shown). [T. Sekido, N. Sakura, Y. Higashi, K. Miya, Y. Nitta, M. Nomura, H. Sawanishi, K. Morito, Y. Masamune, S. Kasugai, K. Yokogawa, K. Miyamoto, Novel drug delivery system to bone using acidic oligopeptide: pharmacokinetic characteristics and pharmacological potential, J. Drug Target. 9 (2001) 111-121] Unlike bisphosphonates and tetracyclines, aspartic acid octapeptide has a low toxicity even in very high concentrations. (Low et al., ibid, Sekido, T. et al., J. Drug Target. 9 (2001) 111-121).

Targeting a drug to a fracture site via aspartic acid octapeptides by itself does not fully exploit the microenvironment of a fracture. In fractured bones, the extent of bone accumulation is expected to be far more dramatic when using large molecules. Yuan et al. (Adv. Drug Deliv. Rev. 64 (2012) 1205-1219) proposed a mechanism by which inflamed tissue leads to leaky vasculature and subsequent inflammatory cell-mediated sequestration (ELVIS). This theory essentially states that large molecules will readily be extravasated from the leaky vasculature of the inflamed fracture callus. Then, inflammatory cells actively phagocytose and sequester any large molecules in the area. (Yuan et al., ibid; Ren, K. et al., Mol. Pharmaceutics 8 (2011) 1043-1051.) Bone fracture calluses certainly fall under the category of inflamed tissue, and as such, higher drug accumulation could hypothetically be achieved by increasing the size of a drug delivery system.

Referring now to FIG. 1, 6BIO is hydrophobic, while the aspartic acid oligopeptide targeting moiety is hydrophilic. Upon addition of aliphatic hydrocarbon chain between 6BIO and the aspartic acid chain a micelle unimer is formed. The micelle increases the overall size of the drug carrier, thereby increasing uptake in the inflamed tissue. Unlike traditional micelles, however, each unimer contains a targeting ligand as well as a drug, ensuring high drug loading. Additionally, should the micelle destabilize in the bloodstream, the drug will remain targeted to the fracture.

Figure 2:
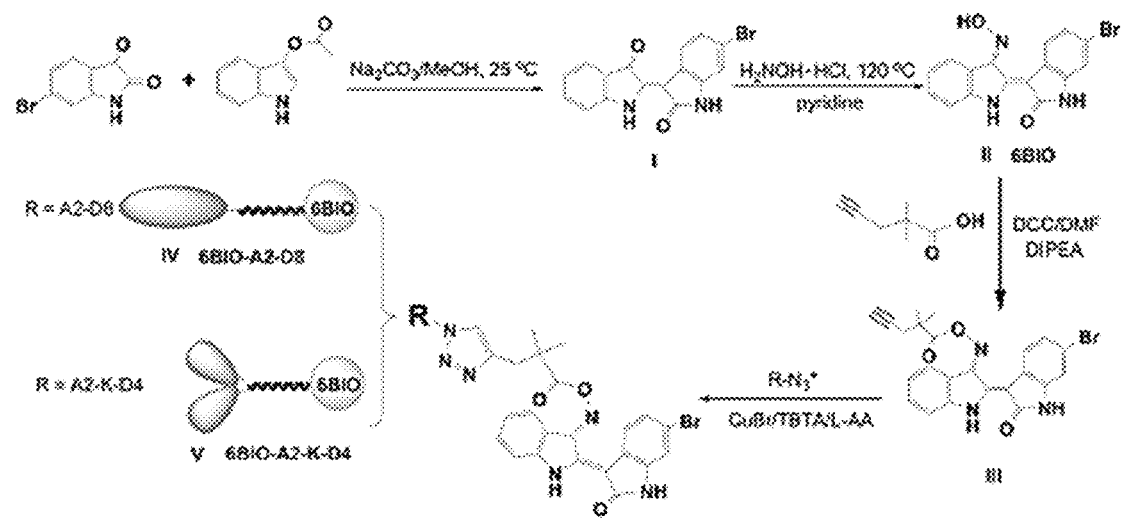
FIG. 2. A schematic diagram illustrating the synthesis of a clickable 6BIO and conjugation of 6BIO and linker to micelle unimers.
Figure 2:
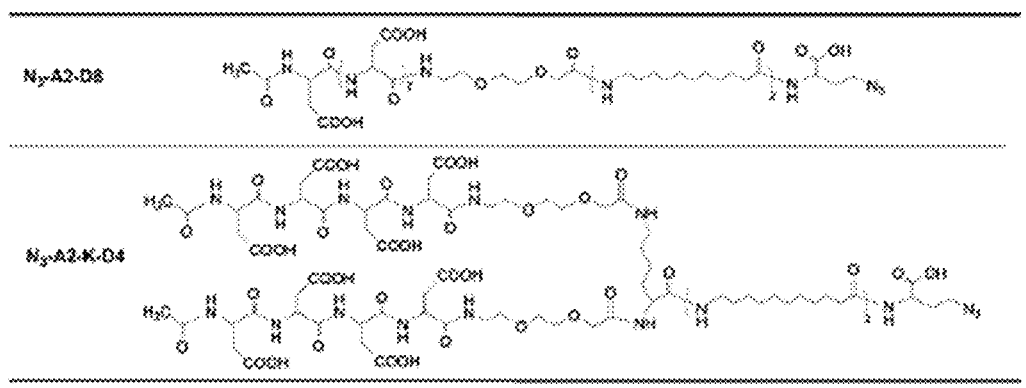

The proposed micellar design is a simplified way of increasing the size of the drug delivery system to increase accumulation in inflamed tissue. Referring now to FIG. 2, by using the hydrophilic targeting peptide aspartic acid octapeptide covalently bound by a hydrolyzable linker to a hydrophobic drug a micelle-forming unimer was created. The designed unimer was largely synthesized using solid-phase peptide synthesis (SPPS). Synthesis began with anazide-containing amino acid (azidohomoalanine) that provided a clickable point of attachment for a drug/linker. To the azide-containing amino acid, two 11-aminoundecanoic acids (AUAs) were attached to increase the hydrophobicity and therefore the stability of the micelle. A miniPEG spacer (8-amino-2,6-dioxaoctanoic acid) was added for flexibility followed by aspartic acid octapeptide for targeting. Finally, the unimer was capped with acetic acid, preventing the terminal primary amine from initiating premature hydrolysis of the amine sensitive drug linker yielding the finalized linear unimer, BIO-A2-D8. BIO-A2-D8 indicates that it is a 6BIO (BIO)-containing unimer with two aminoundecanoic acids (A2) and eight aspartic acids in a linear fashion (D8).

The stability of the micelle can be modified by increasing or decreasing the number of AUAs. However, increasing the number of AUAs in a linear micelle by too much can result in aggregates and non-micellar structures. To increase the number of AUAs and avoid the formation of non-micellar structures, we also studied a branched aspartic acid head group. Building from the original azide-aminoundacanoic acid base, lysine was added to the second aminoundecanoic acid. The both primary amines on the lysine were deprotected and miniPEG was added to both, followed by four aspartic acids each and capping with acetic acid. The 6BIO (BIO) containing unimer contains two aminoundecanoic acids (A2) is branched at the lysine (K) and ends in two branches of four aspartic acids (D4) yielding BIO-A2-K-D4. This branched conformation increased the head group size and therefore the conicity of the unimer. By increasing the head group size, far greater hydrophobic portions could be incorporated before the conicity of the unimer was lost, and a bilayer, aggregate, or other conformation was formed. (Low et al., ibid.)

The designed micelles, in addition to increasing the fracture accumulation by increasing the size, have several unique features. By building the unimers by SPPS, the unimers were monodisperse, which aided in characterization. Furthermore, each unimer featured a targeting ligand and a drug. This means that in the event of the micelle rupturing in the blood stream, the drug still could accumulate in the fracture site by aspartic acid octapeptide-HAp interactions. In addition, whereas many micelles have inconsistent drug loading, the linear and branched micelles contained a consistent 17% or 15% drug loading by weight, respectively.

The drug being attached to the unimers was a GSK3$\beta$ inhibitor, 6BIO. It has been used for increasing osteoblast activity and has an enzymatic IC50 of 5 nmol. (Baron, R. & Rawadi, G., Endocrinology 148 (2007) 2635-2643; Piters, E, et al., Arch. Biochem. Biophys. 473 (2008) 112-116; Krause, U. et al., Proc. Natl. Acad. Sci. USA 107 (2010) 4147-4152). 6BIO by itself, however, is not soluble in water. By including 6BIO in the unimer design, the unimer solubilized the drug while the drug stabilized the micelle. The oxime of 6BIO was first conjugated to the carboxylic group of a 4-pentynoic acid derivative and then clicked to the azide-containing unimer by the alkyne on the 4-pentynoic acid derivative. Upon completion of the click reaction, the micelle was purified, dried, and formed micelles upon reconstitution in PBS.

Figure 3:
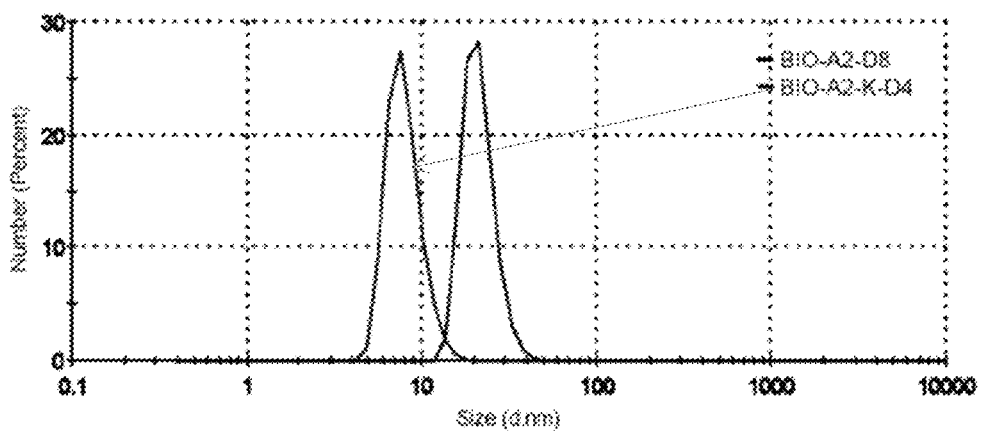
FIG. 3. A graph showing dynamic light scattering of the linear micelle BIO-A2-D8 and the branched micelle BIO-A2-K-D4 in PBS at 25° C.

Size determination by dynamic light scattering. Dynamic light scattering was used to determine the hydrodynamic diameter of the micelles. The micelles self-assembled at the concentrations theorized to be sufficient for injection for fracture healing. BIO-A2-D8 and BIO-A2-K-D4 were 28.8 nm and 11.2 nm respectively (FIG. 3). Sizes were slightly smaller than the micelles with similar structures in our previous work with doxorubicin loaded micelles. (Low et al., ibid).

Figure 4:
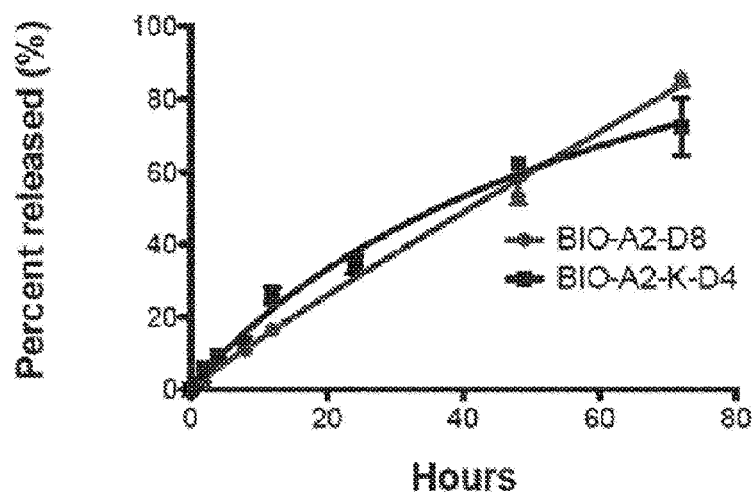
FIG. 4. A graph showing time dependent 6BIO release from the linear micelle BIO-A2-D8 and the branched micelle BIO-A2-K-D4 in PBS at 25° C.

Micellar drug release. Drug-linker selection plays an important role in maintaining targeting ligand to drug integrity until the drug has reached the target tissue. This micelle features an oxime linkage which is base sensitive and hydrolytically cleavable at the pH ranges found in a bone fractures (6.9-7.6). (Swenson, O., J. Bone Joint Surg. Am. 28 (1946) 288-293.) Simple 4-pentynoic oxime esters degrade within hours and would likely release 6BIO prior to fracture accumulation. To improve the hydrolytic stability of the conjugate, germinal dimethyl substituents were introduced into the structure (FIG. 2). This increased steric hindrance to the 107° Bürgi-Dunitz angle required for a Bac2 reaction to release the drug and completely eliminate the possibility of an E1cb reaction. The stabilized oxime ester linkage slowly reached 30% release over 24 h and continued to release over several days (FIG. 4). Though the linker is not specific to the fracture microenvironment, the slow degradation would reduce the amount of drug released in the blood stream prior to fracture accumulation and reduces the frequency of necessary dosing for treatment.

Figure 5:
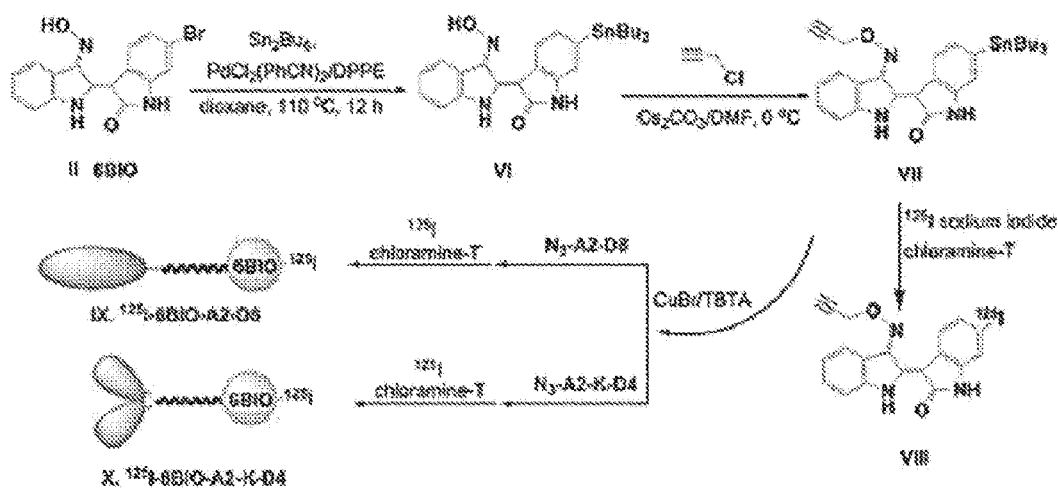
FIG. 5. A schematic diagram illustrating the synthesis of radio-iodinated micelles and 6BIO.

Biodistribution: Organ biodistribution at 24 h. Referring now to FIG. 5, BIO-A2-D8 and BIO-A2-K-D4 have hydrolyzable oxime ester linkages designed to release the 6BIO for treatment of bone fractures. Although a cleavable linker is necessary for therapy studies, it may pose a problem with biodistribution studies. At 24 h of an in vivo study, 30% of the drug may be released. In a biodistribution study, premature release would not give accurate information on how well the targeting ligand is able to remain in the fracture site. A non-degradable oxime ether linker replaced the oxime-ester linker in the micelles for biodistribution. Radiolabeling BIO-A2-D8, BIOA2-K-D4 and 6BIO was done by substituting the bromine on 6BIO with $^{125}$I. These minor modifications allowed the majority of the molecule to remain unmodified while giving information on targeting and free drug clearance.

In bone, HAp increases in crystallinity over time. It is this higher crystalline state to which acidic oligopeptides (AOs) preferentially bind. (Wang et al., ibid; Miller, et al., ibid.) In bone fracture patients, highly active osteoclasts produce extensive resorption surfaces by exposing highly crystalline Hap surfaces to which AOs are able to target. (Schindeler, A. et al., Semin. Cell Dev. Biol. 19 (2008) 459-466.) This specificity to highly crystalline Hap may additionally reduce non-specific binding to the majority of the non-fractured bone. An organ biodistribution was performed to elucidate this and other questions about the fate of the micelles in vivo.

Figure 6:
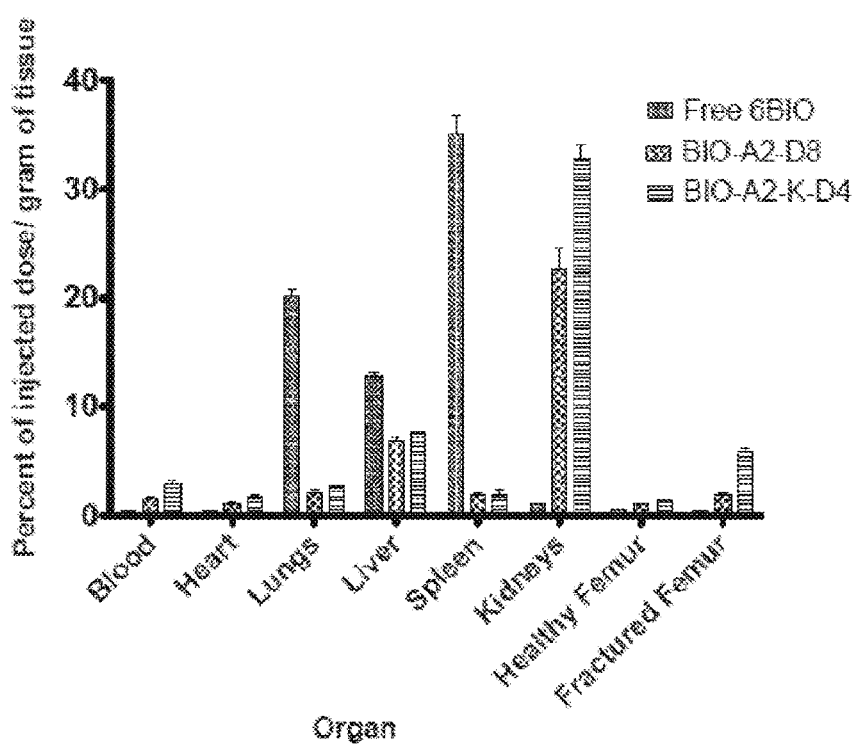
FIG. 6. A bar graph showing the organ distribution of free 6BIO, the linear micelle BIO-A2-D8, and the branched micelle BIO-A2-K-D4 measured in percent of injected dose/gram of tissue.

Several interesting observations emerged from the biodistribution. Referring now to FIG. 6, 6BIO is a hydrophobic drug and its high accumulation in the lungs, liver, and spleen was likely due to the drug aggregating. By turning the drug into an amphiphile, the particle size was controlled, and the liver, spleen, and lung accumulation all decreased significantly ($p<0.001$). However, kidney uptake dramatically increased with both micelles ($p<0.001$). The kidney accumulation may be due to the kidney's ability to recycle peptides such as the aspartic acid octapeptide back into the blood stream. (Kanai, Y. & Hediger, M. A., Nature 360 (1992) 467-471; Ganapathy, M. E. et al., Biochem. Biophys. Res. Commun. 246 (1998) 470-475.) As long as the micelle is not internalized into renal cells, the 6BIO should eventually hydrolyze, be cleared, and not inhibit GSK3$\beta$ expression.

One of the purposes of the study disclosed here was to elucidate the bone and fracture targeting potential of targeted micelles as compared to the free drug, still another purpose was to determine if there were differences in bone fracture healing between branched and linear designs. Naturally, accumulation in healthy femurs was higher in both the linear ($1.0\pm0.27$; $p<0.01$) and the branched ($1.4\pm0.14$; $p<0.001$) micelles than free 6BIO ($0.5\pm0.10$). This is also the first evidence of the branched micelle having a higher accumulation than the linear micelle in bone ($p<0.05$). These trends were amplified when comparing the fractured femurs. The fractured femurs of the free 6BIO, linear, and branched micelles were each statistically different from each other ($p<0.001$) with values of $0.4\pm0.05$, $1.9\pm0.32$, and $6.0\pm0.51$, respectively. Both unimers demonstrated an important increase of accumulation in the fractured femurs over the free drug control.

The micelles were able to show fracture-specific targeting compared to healthy bone. While there was no statistical difference in accumulation of the free drug between the healthy and the fractured femurs, both the linear and the branched micelles showed significantly ($p<0.001$) higher drug uptake in the fractured femur by a 1.8 and a 4.3 fold increase, respectively.

Figure 7:
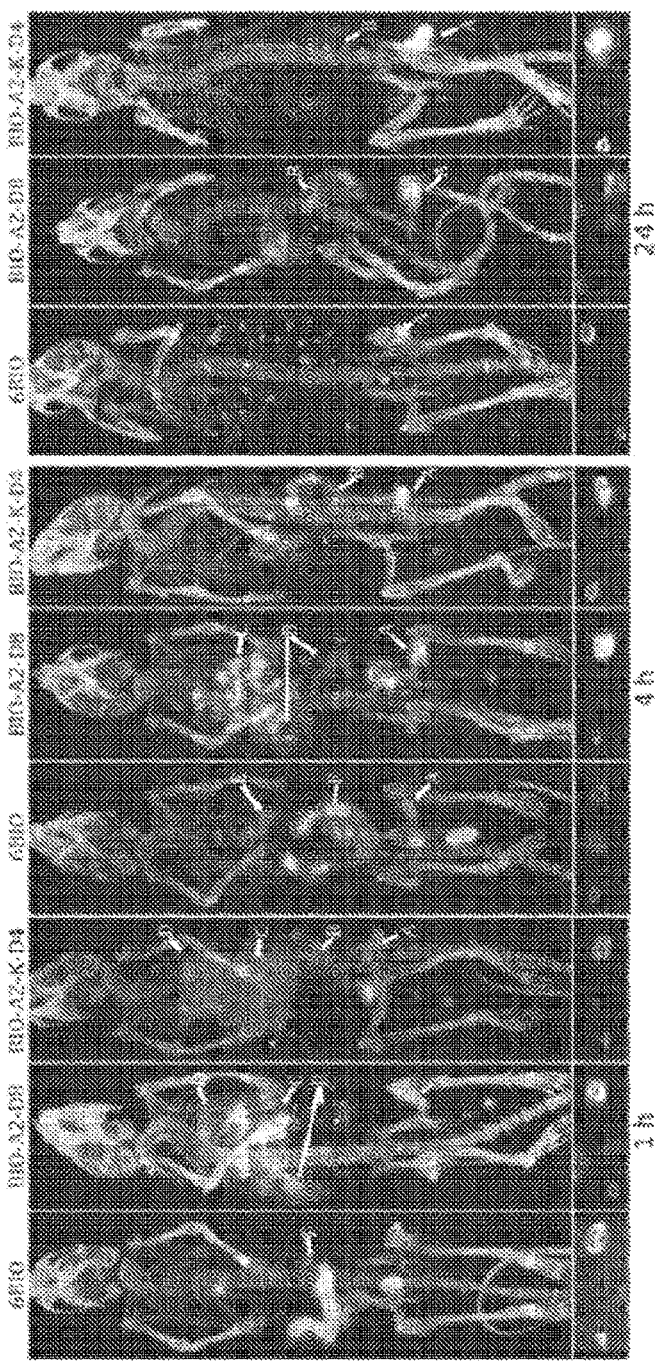
FIG. 7. Photographs of SPECT/CT scan of mice at 1 h, 4 h and 24 h. The upper frames are a 3D reconstruction of the whole mouse. The lower frames are a cross section of the femurs with the fractured femur on the right. Organs are panel A, fracture panel; B, kidneys; C, liver; D, lungs; E, spleen; and F, bowels.

SPECT/CT biodistribution. Referring now to FIG. 7, in order to validate the organ biodistribution and study the clearance of the micelles, SPECT/CT imaging was performed at 1 h, 4 h, and 24 h. In general, fracture-specific uptake was more evident at later time points than earlier ones. At 1 h, a small amount of fracture accumulation was visible in both micelles; however, high signal intensities in both the lungs and kidneys made them difficult to discern. On the other hand, at one hour the free drug was primarily found in the stool. At 4 h, free drug was still primarily contained in the bowel; however, spleen accumulation began to be more evident. Again this bowel uptake was likely due to aggregation of free 6BIO and the resultant uptake by macrophages in the lungs, liver, and spleen resulting in clearance through the bile into the bowels. Meanwhile, the linear micelle had cleared somewhat from the lungs, was still strong in the kidneys, but much more visible in the fracture. The branched unimer showed superior targeting at four hours with the majority of accumulation in the femur and kidneys. At 24 h, free drug appears to be cleared; all signals were background. Both micelles had their highest fracture accumulation intensities at 24 h relative to other organs. Liver to kidney accumulation was lower in the branched unimer, which correlates with the 24-h organ biodistribution data (FIG. 7—24 h compared to FIG. 6). In both micelles throughout the experiment there was no apparent accumulation in the bowels, leading us to believe that most was excreted through urination. Most importantly, there was no noticeable uptake in the healthy bone while the fractured bone had high accumulation.

Between the SPECT data and the organ biodistribution data there were a few discrepancies. Primarily, the high ratio of renal accumulation to fracture accumulation in the organ biodistribution is not as pronounced in the SPECT data. While not wishing to be bound by theory, there are several explanations for this. First, the kidneys contain proteins for the reabsorption of peptides from the urine. It is plausible that peptide kidney transporters were saturated in the SPECT study due to a 100-fold increase in drug dose compared to the organ biodistribution. Bone fracture targeting is not limited by a finite number of receptors as in the kidney; rather, it is limited by the surface area of the bone and may not have been similarly saturated.

In addition, the organ biodistribution is measured in injected dose/gram and does not account for differences in tissue type or location of accumulation within an organ. Bone is far denser (1900 kg/m$^3$) than soft tissue organs such as kidneys or liver (1030-1060 kg/m$^3$). This difference in density dilutes the injected dose/gram measurements in bone compared to an organ such as a kidney. While no hotspots are found in the kidney due to the accumulation being distributed throughout the entire kidney, the signal in fractured femur is further muted by the entire bone being weighed for the measurement rather than the fracture alone. The combination of these factors better explains why in the SPECT study, accumulation per volume is much higher in the fracture compared to the kidney.

In this study two fracture-targeted micelles designed to increase the rate of healing in bone fractures were created. These micelles were built on the concept that the micellar corona can function as both a moiety that gives amphiphilicity, as well as being a low toxicity targeting ligand. Likewise, the 6BIO drug functions both as a pharmaceutical as well as giving stability to the micelle core. The micelles also feature a hydrolysable oxime ester bond to the drug that releases the drug unmodified over several days.

In vivo, both the branched and linear micelle designs demonstrated excellent uptake in fractured bone versus healthy bone. The branched unimer demonstrated both a higher ratio of fracture to kidney uptake as well as fracture to healthy bone accumulation over the linear unimer.

Example 2. Healing Efficacy of Fracture-Targeted GSK3β-Loaded Micelles for Improved Fracture Healing Experimental Procedures Synthesis of unimers. 6BIO and all unimer synthesis was performed as described previously in Example 1. Briefly, micelle 6BIO was conjugated to 2,2-dimethylpent-4-ynoic acid using DCC/DIPEA coupling followed by purification with flash chromatography. Unimers were constructed on chlorotrityl resin using solid phase peptide synthesis starting with Fmoc-Dab(N3)-OH. Each amino acid was added through using HATU/DIPEA coupling and 20% piperidine in DMF for Fmoc deprotection. Unimers were purified using reverse phase HPLC and coupled to the 6BIO linker using copper catalyzed azide-alkyne Huisgen cycloaddition chemistry and were purified using LH20 column chromatography.

Mouse handling. All animal experiments were performed in accordance to Purdue University's IACUC approved protocols. Forty mice (10 per group) 31-35 g male CD4 Swiss Webster mice were purchased from Harlan laboratories. Mice were able to move freely throughout the experiment. At 3 weeks following fracture induction, mice were euthanized using a CO2 overdose. Both fractured and healthy femurs were excised and fixed in formalin solution along with the kidneys and liver. Mice were excluded from the study upon migration of the fracture stabilization pin or an insufficient fracture where the fracture did not pass through the bone.

Mouse bone fracture. A stabilized femoral fracture was performed under aseptic conditions with isoflurane anesthesia. Skin around the knee was shaved and cleaned with alcohol pad first, then with Betadine solution. The skin incision was made over the knee. The patella was then dislocated and a small hole was made under the patella with a 25 guage needle. The needle was used to ream the intramedullary canal. A 22 guage locking nail was produced by flattening both ends was then inserted. The incision site was sutured and the femur was then fractured using a three-point bending device. Buprenorphine (0.05-0.1 mg/kg) was administered subcutaneously at the time of fracture, and dosed every 12 h for 3-7 days post-operation.

Mouse dosing. Mice were dosed intravenously by tail vein injection every 3 days starting on the day of fracture induction. Micelles were reconstituted in sterile PBS while 6BIO was reconstituted in 1% DMSO and PBS. Dosages were calculated assuming 1% fracture accumulation and a 20 nM concentration being necessary to elicit accelerated bone growth for the 5 nM enzymatic IC50 of 6BIO. Mice receiving drug dosages were administered drugs at the follow dose 6.9 nmol/kg/dose in approximately 0.1 mL of PBS. PBS control mice received 0.1 mL of PBS.

μCT analysis. Scanco μCT 40 was used to collect CT images and data of bone. The bones were scanned while immersed in PBS to prevent dehydration. Scanco μCT software was used to analyze the images for bone density, total volume (TV), relative bone volume (BV/TV), trabecular thickness (Tb.Th), and trabecular spacing (Tb.Sp). Volumes of interest included the fracture callus, and both cortical and trabecular bone between the points on the cortical bone where the bone was fractured.

Images. Images collected from the μCT were studied using Image J software. Average pixel of a 3-dimensional reconstruction of a 50 slices stack were used and represent approximately 0.3 mm of tissue in depth. Minimum brightness threshold was adjusted to 4273 on all images to eliminate non-calcified tissue from view.

Statistical analysis. Statistical analyses were calculated using Prism GraphPad software. Data is presented in results as mean±standard error of the mean (SEM). An unpaired student's t-test was used to determine statistical significance with P values less than 0.05 being considered statistically significant.

Slide preparation. Tissues were fixed in PBS buffered formalin solution for at least 24 h. Following fixation, tissues were embedded in paraffin, sectioned, and floated on slide. Slides were deparaffinized and rehydrated for staining.

Figure 8:
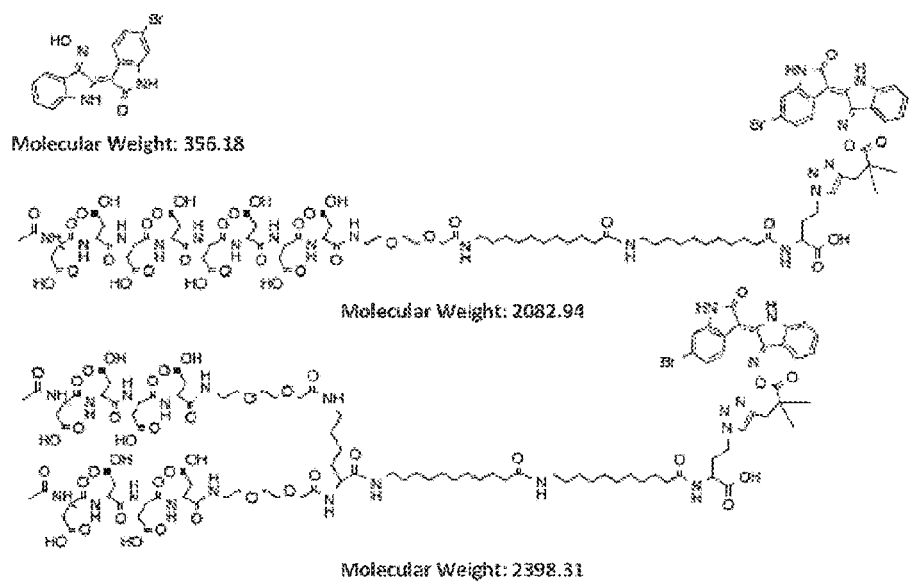
FIG. 8. A schematic showing the structures of 6BIO (top), linear BIO-A2-D8 (middle), and branched BIO-A2-K-D4 (bottom).

Results: Two micelles designed to improve fracture healing in long bone fractures have been developed. Previous studies of the micelles demonstrated their specificity to bone fractures. Here, we tested the healing efficacy and biocompatibility of the micelles. The first of the micelles is composed of a linear unimer design. (Example 1; Low et al., ibid.) The drug, 6BIO, was conjugated to 2,2-dimethyl-3-butynoic acid by DCC/DIPEA coupling. The 6BIO plus linker was then conjugated by copper catalyzed azide-alkyne Huisgen cycloaddition to a unimer built using solid phase peptide synthesis. Referring now to FIG. 8, the unimer was assembled starting with azidohomoalanine followed by two aminoundecanoic acids (A2), miniPEG (8-amino-3,6-dioxaoctanoic acid), eight aspartic acids (D8) and capped with acetic acid yielding BIO-A2-D8. BIO-A2-D8 features a targeting ligand that, upon micellar assembly, acts as the corona of the micelle. 6BIO is hydrophobic and acts both as the drug and the core of the micelle, increasing the micelle's stability. Micelles gain their stability from hydrophobic interactions, so adding additional aminoundecanoic acids will make the micelle more stable. (Low et al., ibid) Addition of too many aminoundecanoic acids, however, causes the unimers to aggregate in non-micellar structures. (Example 1; Low et al., ibid.) To circumvent this, a branched head group unimer was designed that increases conicity of the unimer. (Low et al., ibid.) The basic assembly was analogous to the linear unimer; however, following the two aminoundecanoic acids (A2), a lysine (K) was added that had both primary amines unprotected, providing two branches. From the lysine, miniPEG was added, followed by four aspartic acids per arm (D4), and was capped with acetic acid, yielding the branched unimer BIO-A2-K-D4 (FIG. 8). BIO-A2-K-D4 contains a total of eight aspartic acids like the linear BIO-A2-D8 but is capable of being further stabilized with several additional aminoundecanoic acids while retaining a micellar structure.

6BIO provided a good candidate drug for a therapy study due to its hydrophobicity as well as its excellent suppression of GSK33. Wnt works by inducing mesenchymal stem cells to differentiate into pre-osteoblasts. The continual activation of the preosteoblasts by Wnt leads to differentiated, active osteoblasts. This means that as long as Wnt is active in the general fracture area, osteoblasts will continually be produced and active. This is evident in fracture healing as Wnt expression peaks during days 3-5 and decreases between 14 and 21 days post-fracture. Previous studies on GSK3-inhibitor treatment of fractures have been successful by extending and amplifying Wnt expression, starting treatment on the day of fracture and continuing dosing on a daily basis until the end of the experiment. (Sisask, G. et al., Bone 54 (2013) 126-132.) Similarly, in this experiment we elevate Wnt signaling over entirety of the experiment. However, the oxime ester bond in our micellar system delivered drug over 3 days reducing administration by tail vein on every third day possible.

Figure 9:
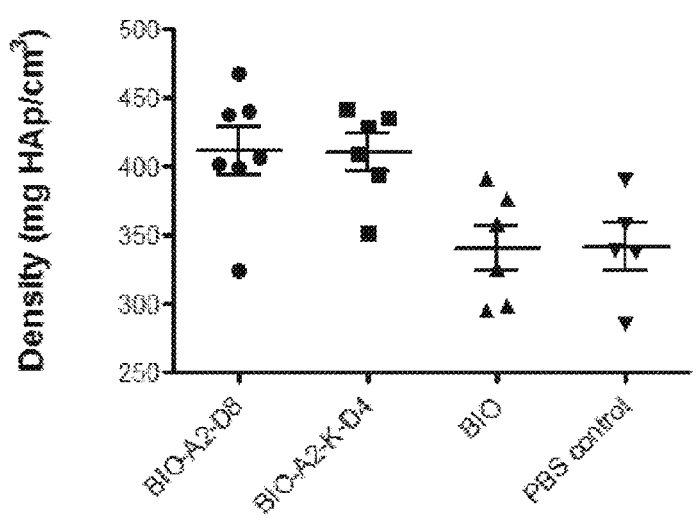
FIG. 9. A graph showing the densities of fracture callus [mg HAp/cm$^3$]. Both unimers are statically different than the free 6BIO and PBS control.

The study was designed to replicate aged fractures while minimizing variance. In order to best simulate an aged fracture, mature CD4 Swiss Webster mice (31-35 g) were used. Potential variance was mitigated by using male mice. Estrogen levels play a significant role in bone growth with large changes in estrogen levels and bone densities occurring at pregnancy, lactation, and menopause. Although these variations of estrogen levels are often associated with long-term changes in bone densities there is evidence that estrogen levels can have dramatic effects with acute variations in estrogen, potentially correlating with estrous cycles.

μCT analysis: Upon completion of the study, femurs were harvested and underwent μCT testing. Information about the bone density, fracture volume, and callus structure were analyzed and used in determining efficacy of the treatment regimen. Bone density is an important tool for assessing bone healing, giving information about cellular activity as well as changes in structural integrity. Bone density was calculated from the mass of the hydroxyapatite (HAp) mineralized part of the fracture callus per unit of the total volume of the fracture callus. The linear and branched micelles yielded 411.1±17.3 mg HAp/cm$^3$ and 409.7±13.8 mg HAp/cm$^3$, respectively, and were significantly higher than the free 6BIO and PBS control, which were 337.8±14.2 mg HAp/cm$^3$ and 348.6±22.7 mg HAp/cm$^3$, respectively (FIG. 9). This overall increase of bone density in the treated micelles over the controls indicated both activity of the micelle-released 6BIO in vivo as well as targeted accumulation in the bone. Although previous studies demonstrated a 2 fold increase in fracture accumulation of the branched micelle over the linear micelle, the resultant bone densities of the linear and branched micelle treatments were not significantly different from each. Also of note, the PBS control and free drug did not differ significantly, indicating that the dose chosen for the study was lower than the amount needed for free 6BIO to initiate bone anabolism.

The relative bone volume (BV/TV) is the mineralized volume of the total volume and is a similar measurement to bone density. Completing the trend observed by the bone density, the micelles outperformed the controls significantly. The BV/TV of the linear micelle BIO-A2-D8 was 0.409±0.019 and branched micelle BIO-A2-K-D4 was 0.409±0.011, while the free 6BIO was 0.338±0.015 and PBS control was 0.332±0.021 (Table 1).

TABLE 1

Comparison of bone morphometric analysis.

| Direct Model | Linear | Branched | Free 6BIO | PBS |
|---|---|---|---|---|
| TV [mm$^3$] | 60.8 ± 3.4 $^{f,p}$ | 66.9 ± 6.8 $^{f,p}$ | 48.2 ± 5.8 | 44.1 ± 8.8 |
| BV/TV | 0.409 ± 0.019 $^{f,p}$ | 0.409 ± 0.011 $^{f,p}$ | 0.338 ± 0.015 | 0.332 ± 0.021 |

TABLE 1-continued

Comparison of bone morphometric analysis.

| Direct Model | Linear | Branched | Free 6BIO | PBS |
|---|---|---|---|---|
| Tb. Th[mm] | 0.175 ± 0.011 $^{f,p}$ | 0.170 ± 0.007 $^{f,p}$ | 0.134 ± 0.007 | 0.139 ± 0.014 |
| Tb. Sp[mm] | 0.208 ± 0.003p | 0.190 ± 0.004 | 0.191 ± 0.009 | 0.181 ± 0.004 |

$^f$ unimer statistically different than free drug
$^p$ unimer statistically different than PBS control The differences in bone densities can be explained partly by measured differences in the bone architecture. Trabecular thickness (Tb.Th) is a measurement of the thickness of all of the mineralized trabeculae. Greater Tb.Th is indicative of a more robust osteoblast population. (Hildebrand, T. et al., J. Bone Miner. Res. 14 (1999) 1167-1174; Parfitt, A. M., Calcif. Tissue Int. 36 (1984) S123-S128.) The BIO-A2-D8 and BIO-A2-K-D4 values were 0.175±0.011 mm and 0.170±0.007 mm, respectively, and again significantly higher than the free 6BIO and PBS control, which were 0.134±0.007 mm and 0.139±0.014 mm, respectively.

The converse of Tb.Th, the trabecular spacing (Tb.Sp), is a deleterious attribute that measures the distances of non-calcified portions of bone between the calcified portions. (Hildebrand et al., ibid.) Little difference between the samples was observed. The only significant difference was the BIO-A2-D8 (0.208±0.003 mm) having an increase in spacing over the PBS control (0.181±0.004 mm). By comparing Tb.Th to Tb.Sp it is evident that the greatest contribution to bone density is produced by the thickness of the trabeculae.

In addition to the densities and microstructure of the callus, larger callus volumes are associated with improved mechanical properties. The callus volume is calculated from the total volume (TV) occupied by both calcified bone and soft tissue. The BIO-A2-D8 and BIO-A2-K-D4 micelles had TVs of 60.8±3.4 mm$^3$ and 66.9±6.8 mm$^3$, respectively, while the free 6BIO and PBS control were 48.2±5.8 mm$^3$ and 44.1±8.8 mm$^3$, respectively. The combination of a significantly larger callus volume and increased bone density are clinically important signs that the targeted micelles are working.

Figure 10:
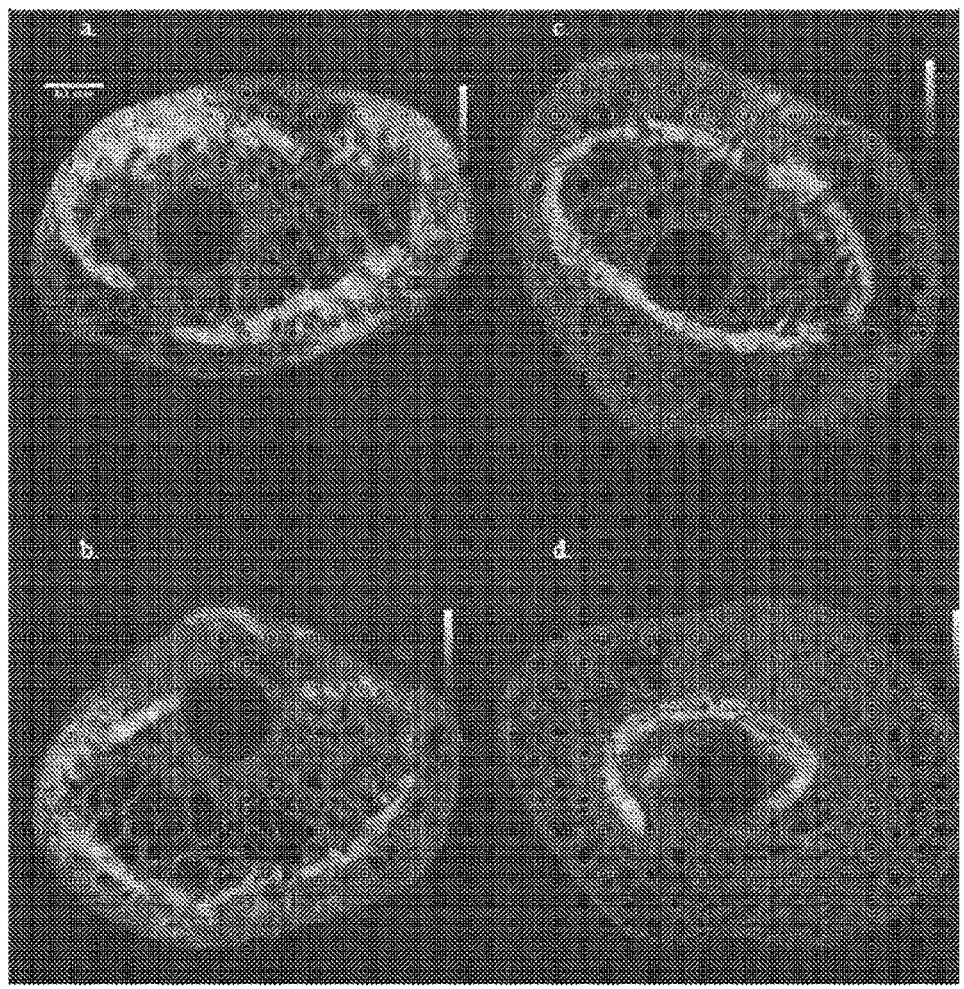
FIG. 10. Photographs of CT scan showing the average composite of fifty 6 µm (0.3 mm) slices: panel a, linear; panel b, branched; panel c, free 6BIO; and panel d, PBS control.

During the fracture healing process the original cortical bone undergoes remodeling by degradation and replacement with new bone. Under extreme GSK3β inhibition, remodeling favors osteoblasts and osteopetrosis may occur. While not wishing to be bound by theory, it is unclear whether GSK3β inhibition resulting in osteopetrosis is a result of systemic inhibition of osteoclasts and whether local GSK3β inhibition will inhibit local favorable catabolism. Referring now to FIG. 10, transverse μCT sections 0.3 μm thick revealed that in both the micelle groups, the original cortical bone has undergone a great deal of remodeling, indicating that dosages were either not high enough to suppress local osteoclast activity or migration of osteoclasts into the fracture was sufficient to overcome local suppression. Evidence of remodeling appears to be greater in the targeted micelles over the controls as the lines differentiating between the original cortical bone and the fracture callus are difficult to discern in many places.

Figure 11:
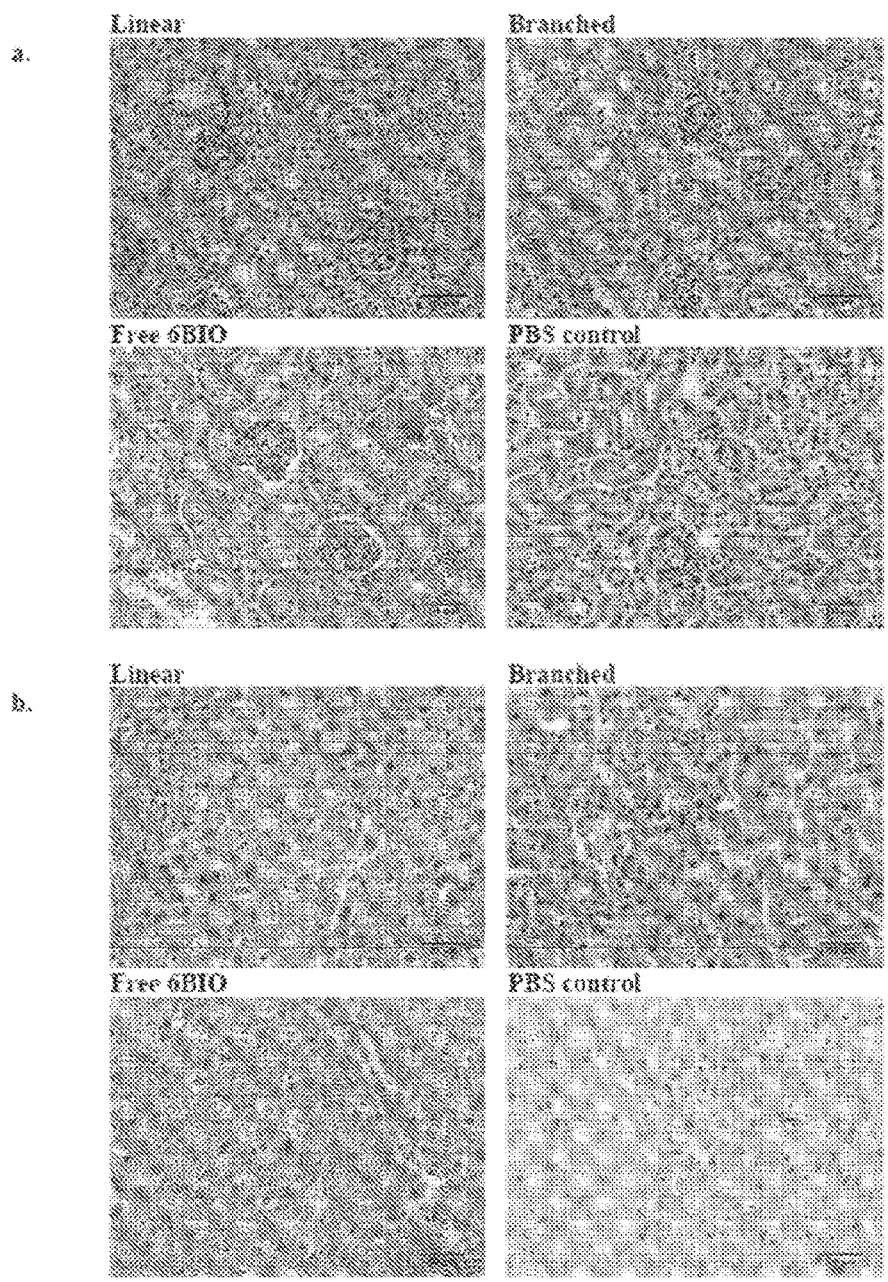
FIG. 11. Photographs showing the histology sections of BIO-A2-D8, BIO-A2-K-D4, 6BIO, and PBS control of panel a, kidney H&E stain; panel b, liver H&E stain.

Histology of kidneys and liver: Referring now to FIG. 11, biodistribution studies showed high uptake in the lungs, liver and kidneys compared to the fracture in both micelle groups at 1 h. By 4 h, both micelle groups demonstrated high uptake in the femurs. The linear micelle still had high uptake in the liver and kidneys while the branched micelle had only high kidney uptake. By 24 h both micelles demonstrated high signals in the femurs. (see Example 1.) In this study, liver and kidneys were harvested. Liver sections showed no evident liver toxicity in morphology or cell concentrations (FIG. 11b). Some potential kidney toxicity was visible in the drug groups where slight glomerular constriction and cell accumulation was evident but data was inconclusive as to whether damage would significantly hinder kidney function (FIG. 11a).

Accelerated fracture healing by targeting the GSK3β inhibitor, 6BIO, to the fracture site has been demonstrated. Both fracture bone mineral density and volume were significantly higher in the micelle treatment groups over both the free 6BIO and PBS controls. Both micelles performed relatively well in the tissues analyzed for toxicity.

Example 3. Efficacy of Fracture-Targeted PGE1 Loaded Compounds as a Treatment for Bone Fracture Prostaglandin E1 (PGE1) can be targeted to help bone grow using a D-aspartic acid oligopeptide. Further, aspartic acid oligopeptides preferentially target the hydroxyapatite in a bone that has turned into large crystals. However, the new growth hydroxyapatite crystals in a bone fracture are small, and therefore, it is unclear whether adequate targeting would occur. In addition, PGE1 is an inflammatory cytokine, which in osteoporosis is necessary to get bone growth started. In the case of bone fractures there is already inflammation and it is unclear if adding a pro-inflamatory cytokine would help or cause too much inflammation may inhibit bone growth and cause catabolism.

For more information, see US Patent Publication No. 2005/0287114, U.S. Pat. No. 6,455,495 and International Patent Application No. WO 1992/020371, disclosures of which are incorporated by reference in its entirety to the extent they are not inconsistent with the explicit teachings of this specification.

Synthesis of PGE1 spacer MA-Gy-Gy-Pro-Nle-4AB. N-(1-((4-(hydroxymethyl)phenyl)amino)-1-oxohexan-2-yl)-1-(methacryloylglycylglycyl)pyrrolidine-2-carboxamide (MA-Gly-Gly-Pro-Nle-4AB) was synthesized using traditional fmoc protected solid phase peptide synthesis on chlorotrityl resin. MA-Gly-Gly-Pro-Nle-4AB was cleaved from the resin using 1% trifluoroacetic acid in DCM.

Conjugation of PGE1 to MA-Gy-Gy-Pro-Nle-4AB. MA-Gy-Gy-Pro-Nle-4AB (22.6 mg, 0.044 mmol), 4-dimethylaminopyridine (DMAP 3 mg), and were dissolved in Dichloromethane (DCM). Prostaglandin E1 (PGE1 20 mg, 0.056 mmol) was also dissolved in DCM, cooled to 0° C., and combine with the MA-Gy-Gy-Pro-Nle-4AB solution. N,N'-Dicyclohexylcarbodiimide (DCC 40 mg, 0.2 mmol) was dissolved in DCM and added dropwise to the PGE1 solution. The solution was stirred overnight at 4° C., filtered and concentrated by evaporation prior to HPLC purification. The resultant 4-(2-(1-(methacryloylglycylglycyl)pyrrolidine-2-carboxamido)hexanamido)benzyl (E)-7-(3-hydroxy-2-(3-hydroxyoct-1-en-1-yl)-5-oxocyclopentyl)heptanoate (MA-Gly-Gly-Pro-Nle-4AB-PGE1) was used later in RAFT polymerization. The structure of a purified MA-Gly-Gly-Pro-Nle-4AB-PGE1 was confirmed using HPLC, Mass Spectrometry, and NMR (data not shown).

Synthesis of MA-Gly-Gly-MiniPEG-(D-Asp)$_8$-OH. (2-(2-(2-(2-(2-methacrylamidoacetamido)acetamido)ethoxy)ethoxy)acetyl)aspartylaspartylaspartylaspartylaspartylaspartylaspartylaspartic acid (MA-Gly-Gly-MiniPEG-(D-Asp)$_8$-OH) was made by standard Fmoc protected solid phase synthesis using D-Aspartic acids. Upon completion the product was cleaved using 95:2.5:2.5 TFA: TIS: H2O, precipitated in diethyl ether, and used without further purification. The structure of a purified MA-Gly-MA-Gly-Gly-MiniPEG-(D-Asp)$_8$-OH was confirmed using HPLC, Mass Spectrometry, and NMR (data not shown).

Synthesis of MA-FITC. Fluorocine isothyocyanate (FITC) was combine with MA-AP (2:1) and dissolved in DMF an excess of DIPEA in DMF was added dropwise. The reaction mixture was stirred at 4° C. for 2 days in dark. Water was added and adjusted to pH~4 by 6 M HCl. The product, 2-(6-hydroxy-3-oxo-3H-xanthen-9-yl)-5-(3-(3-methacrylamidopropyl)thioureido)benzoic acid (MA-FITC) was filtered and washed with water and dried under reduced pressure.

Figure 12:
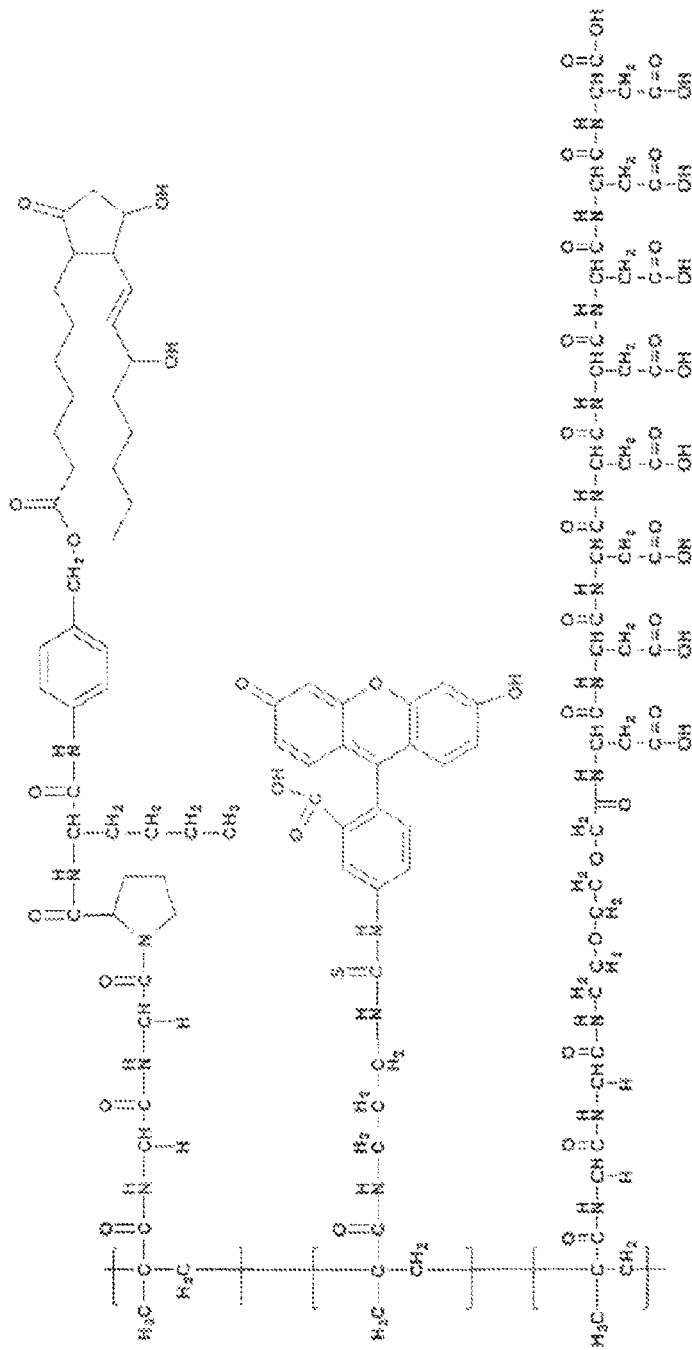
FIG. 12. A structure of a functionalized polymer.

Polymerization. Referring now to FIG. 12, MA-FITC (2 mol %), MA-Gly-Gly-MiniPEG-(D-Asp)$_8$-OH (3 mol %), MA-Gly-Gly-Pro-Nle-4AB-PGE1 (5 mol %), and N-(2-Hydroxypropyl) methacrylamide ("HPMA monomer") (90 mol %) were dissolved in methanol and trasfered to a small ampule. AIBN and chain transfer agent were added to the solution. The solution was bubbled with nitrogen for 20 minutes, the ampule sealed, and placed in a 45° C. waterbath for 72 hours. The product was precipitated in acetone.

Mouse experiment. Swiss mice acquired from Harlan laboratories were used for these experiments. A stabilized femoral fracture was performed under aseptic conditions with isoflurane anesthesia. Skin around the knee was shaved and cleaned with an alcohol pad first, then with Betadine solution. The skin incision was made medial parapatellar. The patella was then dislocated and an incision was made under the patella. A 25 gauge needle was used to ream the intramedullary canal. A 22 gauge locking nail (where both ends are flattened to produce rotational stability), was then inserted. The wound was sutured and the bone was then fractured using a three point bending device that has a built-in stop to prevent excess injury. Subcutaneous Buprenorphine (0.05-0.1 mg/kg) was administered at the time of surgery, followed by a dose every 12 h for 3-7 days post operation.

Figure 13:
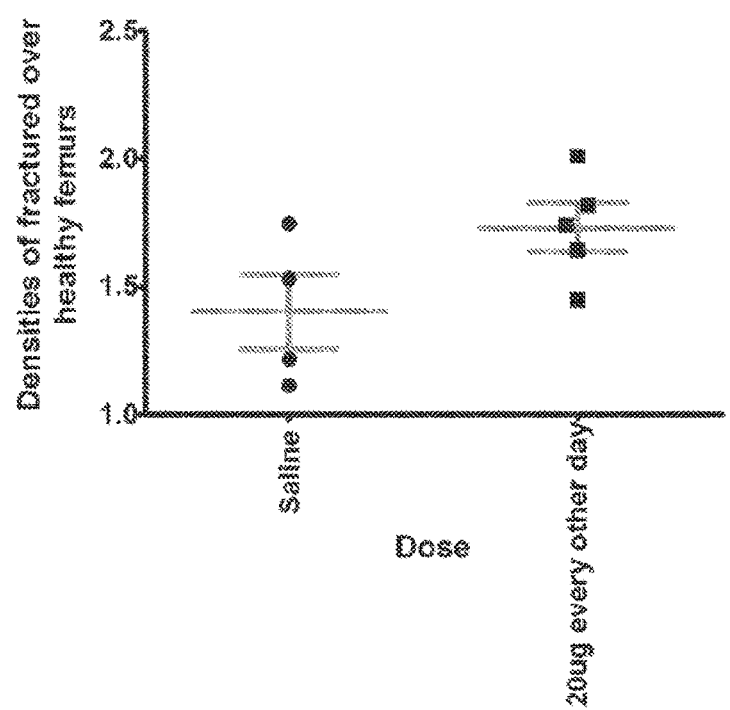
FIG. 13. A graph showing densities of fractured femurs upon treatment with a control (saline) or 0.4 mg polymer solution (20 µg prostaglandin).

Mice were dosed every other day with 0.4 mg (20 ug prostaglandin) polymer solution or with saline throughout the experiment. Mice were sacrificed 5 weeks following fracture induction. Femurs were harvested and bone densities were measured using a DEXA machine. Referring now to FIG. 13, the resultant bone densities of the polymer treatments were significantly higher than that of the control (P<0.05; one-tailed).

Following DEXA analysis bones from mice were scraped and fixed. The bones were placed in 3 consecutive solutions of methylmethacrylate with increasing concentrations of catalyst. In the third solution excess air was vacuumed out of each solution in order to ensure consistent bone slices. Each bone was set in a separate 20 ml glass vial. The solution was allowed to set in a warm water bath. Once the solution polymerized each vial was crushed, excess polymer was trimmed off using a grinder and the bone was sliced into several thin slices. The slices were then mounted onto plastic slides and pressed overnight in vice grips. Each slice was then sanded and polished down using a rotating water sander and polisher.

Figure 14:
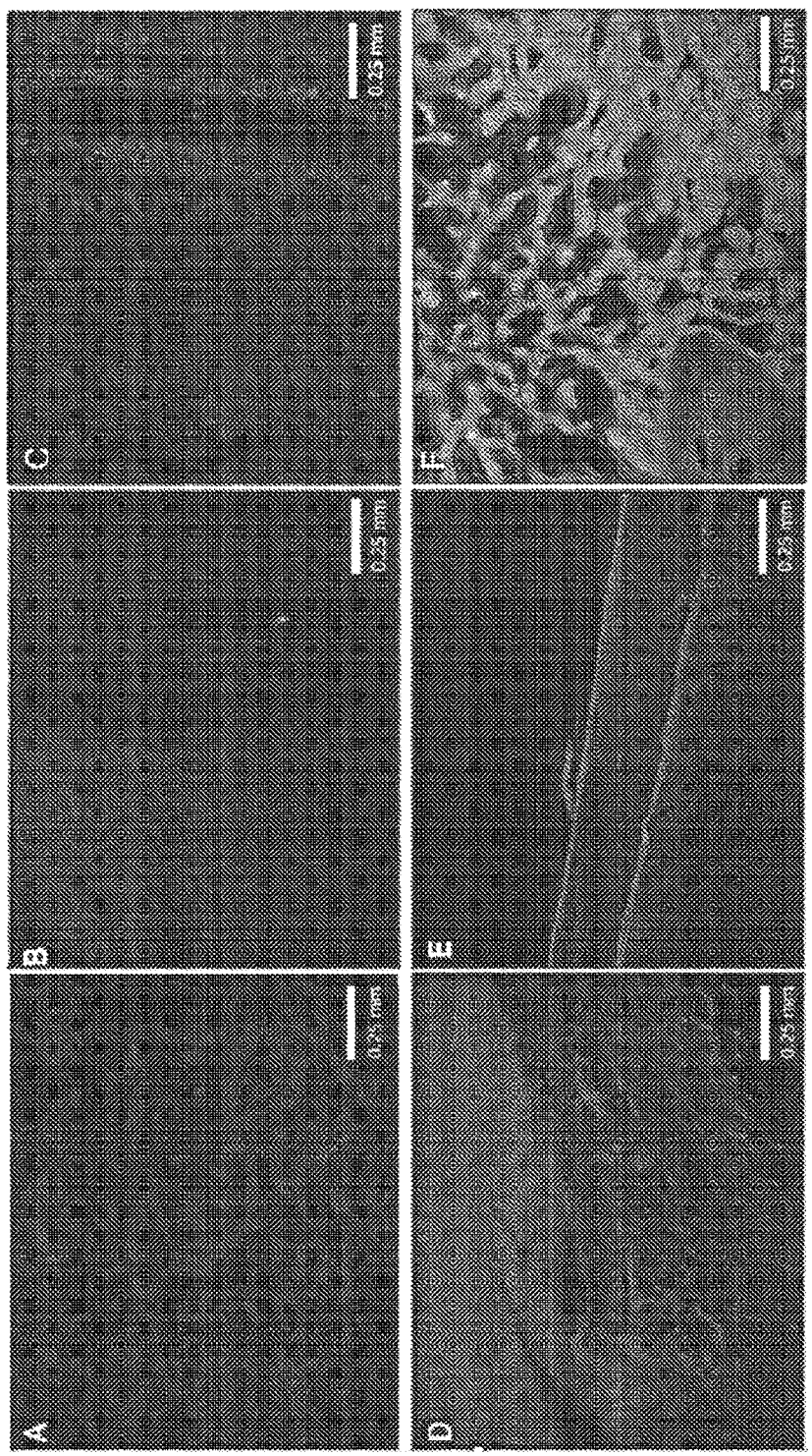
FIG. 14. Photographs showing the uptake of aspartic acid octapeptide targeted HPMA copolymer (P-PGE1-Asp$_8$-FITC) under identical magnifications in: panel A, fracture callus (vehicle control); panel B, skull (P-PGE1-Asp$_8$-FITC); panel C, vertebrae (P-PGE1-Asp$_8$-FITC); panel D, paw (P-PGE1-Asp$_8$-FITC); panel E, healthy femur (P-PGE1-Asp$_8$-FITC); and panel F, fracture callus (P-PGE1-Asp$_8$-FITC).
Figure 15:
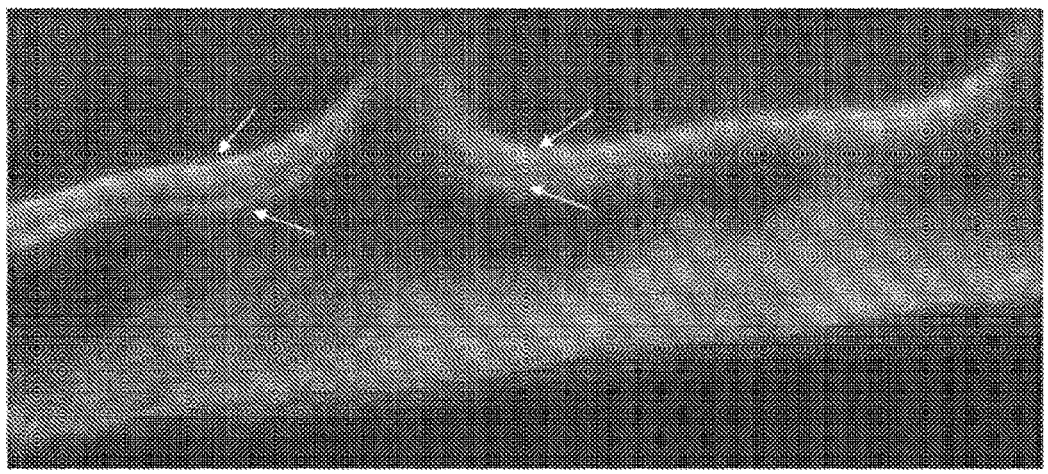
FIG. 15. A photograph showing several layers of deposited FITC labeled polymer (white arrows).

Referring now to FIG. 14, the uptake of aspartic acid octapeptide targeted HPMA copolymer (P-PGE1-ASP-FITC) was evident in paw (FIG. 14D), healthy femur (FIG. 14E), and fractured callus (FIG. 14F) of treated mice. Fractured callus showed a marked increase in uptake of P-PGE1-ASP$_8$-FITC when compared to other parts of the bone (FIG. 14F). Referring now to FIG. 15, several layers of deposited FITC labeled polymer can be seen (white arrows).

Figure 16:
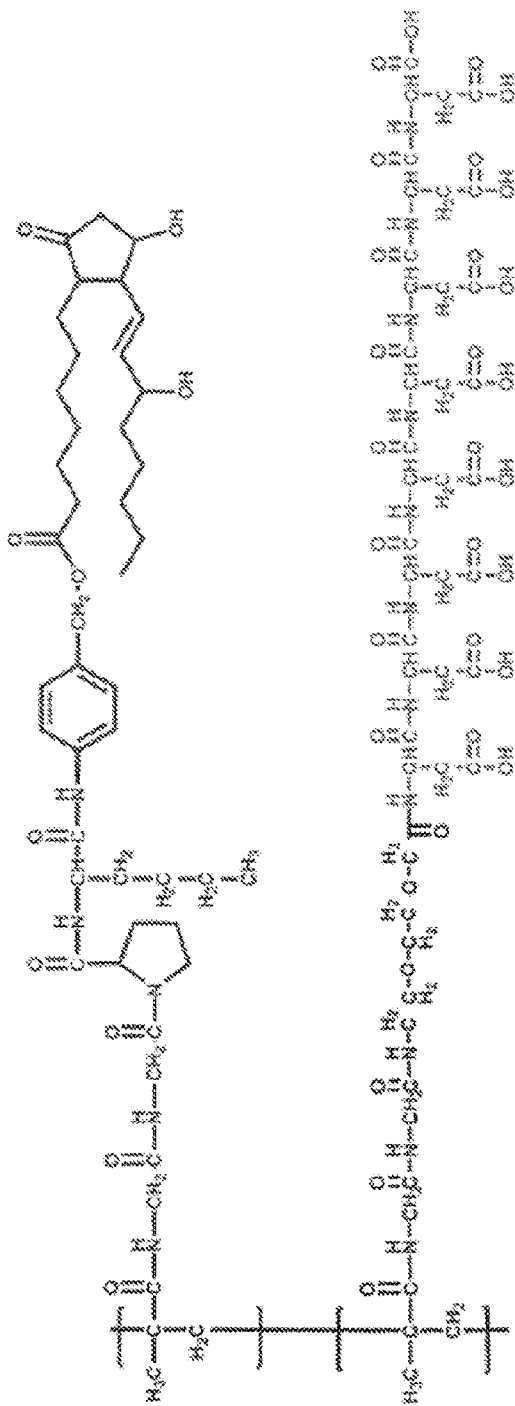
FIG. 16. A structure of a polymer ("P-PGE1-Asp$_8$").

Synthesis of P-PGE1-Asp$_8$. Referring now to FIG. 16, MA-Gy-Gy-MiniPEG-(D-Asp)$_8$-OH (3 mol %), MA-Gly-Gly-Pro-Nle-4AB-PGE1 (5 mol %), and HPMA monomer (92 mol %) were dissolved in methanol and transferred to a small ampule. AIBN and chain transfer agent were added to the solution. The solution was bubbled with nitrogen for 20 minutes, the ampule sealed, and placed in a 45° C. water bath for 72 hours. The product was precipitated in acetone.

Male retired breeder Sprague-Dawley rats having an average weight of approximately 670 g were used for these experiments. A stabilized femoral fracture was performed under aseptic conditions under anesthesia of Ketamine (100 mg/ml)/Xylazine (20 mg/ml) in 1:1 mixture, 0.1 ml/100 g body weight. Skin around the knee was shaved and cleaned with alcohol pad first, then with Betadine solution. The skin incision can be made medial parapatellar. The patella was then dislocated and a incision was then made under the patella. A guide wire, 0.1 mm in diameter was inserted into the intramedullary canal. The bone was then fractured using a three point bending device. A locking nail, 0.55 mm was inserted over the guide wire. The guide wire was removed and the nail is secured in place with a wedge to prevent migration of the nail post operation. The wound was stitched. Buprenorphine (0.05 mg/kg) was administered at the time of surgery, followed by a dose every 12 hours for four days post operation.

Rats were dosed at the time of fracture and every $3^{rd}$ day following with saline, 12.5 µg/kg PGE1, 125 µg/kg PGE1 (both test dosages were targeted polymer form of PGE1, dosages were calculated by the mol % PGE1 in the polymer) for a total of 8 doses. In total the test groups received the equivalent of 100 µg/kg and 1000 µg/kg of PGE1 over the course of the experiment. Rats were euthanized 39 days following fracture induction and femurs were excised.

Figure 17:
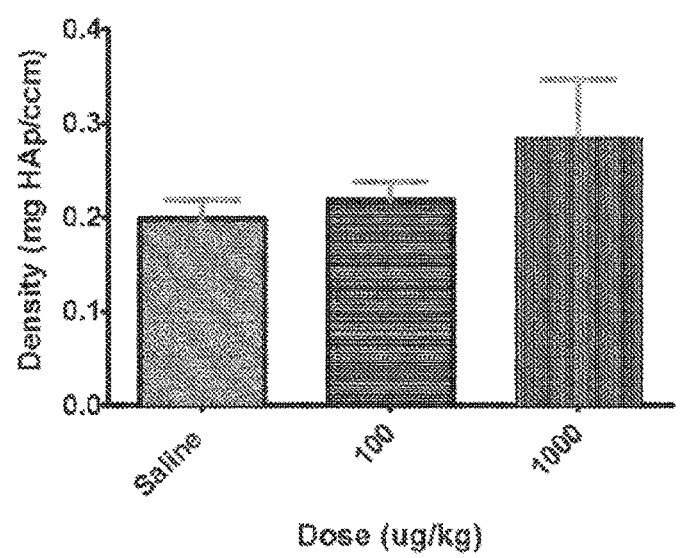
FIG. 17. A bar graph showing bone fracture densities of the rat upon treatment with various doses of a polymer ("P-PGE1-Asp$_8$").

Referring now to FIG. 17, rats receiving higher dosage (1000 µg/kg) exhibited increased bone density when compared to the control (saline).

While the novel technology has been illustrated and described in detail in the figures and foregoing description, the same is to be considered as illustrative and not restrictive in character, it being understood that only the preferred embodiments have been shown and described and that all changes and modifications that come within the spirit of the novel technology are desired to be protected. As well, while the novel technology was illustrated using specific examples, theoretical arguments, accounts, and illustrations, these illustrations and the accompanying discussion should by no means be interpreted as limiting the technology. All patents, patent applications, and references to texts, scientific treatises, publications, and the like referenced in this application are incorporated herein by reference in their entirety.

We claim:

1. A method of treating a bone fracture, comprising the step of:
   administering to a patient suffering from the bone fracture a therapeutic amount of a compound of the formula, A-B-(MA)$_n$-C-D, wherein:
   A is at least one negatively charged oligopeptide;
   B is a spacer;
   C is a linker having the formula:

-Gly-Gly-Pro-Xle wherein:
   Gly is a glycine;
   Pro is a proline; and
   Xle comprises at least one moiety selected from the group consisting of norleucine, leucine, isoleucine, a hydrophobic amino acid, and an amphipathic amino acid;
   D is an active compound that promotes the healing of bone fractures selected from prostaglandin E1 or prostaglandin E2;
   MA is a backbone structure which is linked to both B and C, wherein MA comprises at least one N-(2-Hydroxypropyl) methacrylamide; and
   n is 1 to 1000.

2. The method of claim 1, further comprising the step of: identifying a patient having a bone fracture.

3. The method of claim 1, wherein A is an acidic oligopeptide.

4. The method of claim 3, wherein the acidic oligopeptide comprises not less than and not more than 20 amino acids.

5. The method of claim 3, wherein the acidic oligopeptide comprises one or more amino acids selected from the group consisting of D-aspartic acid, L-aspartic acid, D-glutamic acid, and L-glutamic acid.

6. The method of claim 1, wherein B is a spacer comprising at least one glycine and at least one 8-amino-2,6-dioxaoctanoic acid.

7. The method of claim 1, wherein C comprises at least one glycine.

8. The method of claim 1, wherein D is prostaglandin E1.

9. The method of claim 1, wherein the compound of the formula A-B-(MA)$_n$-C-D is:

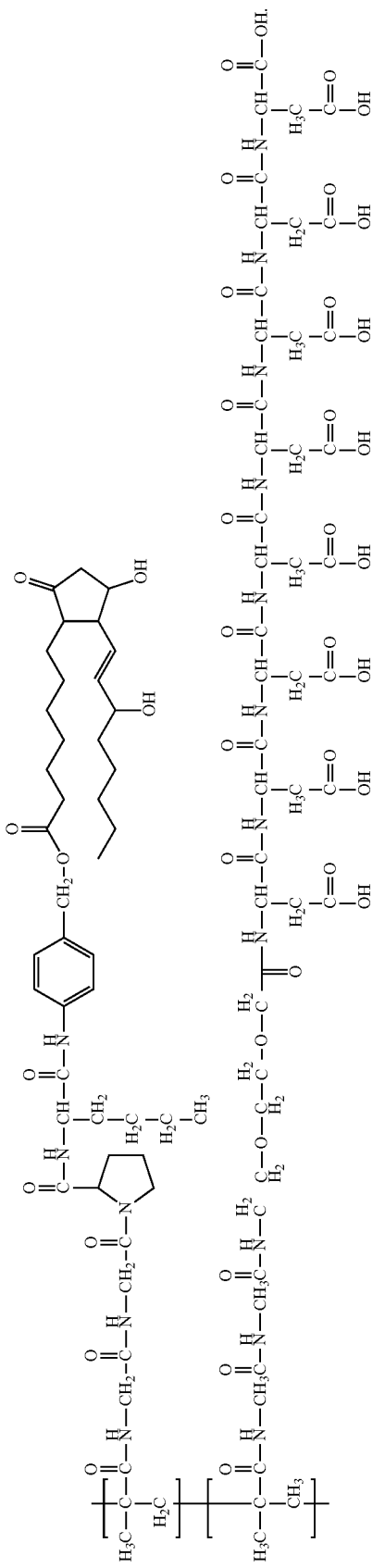
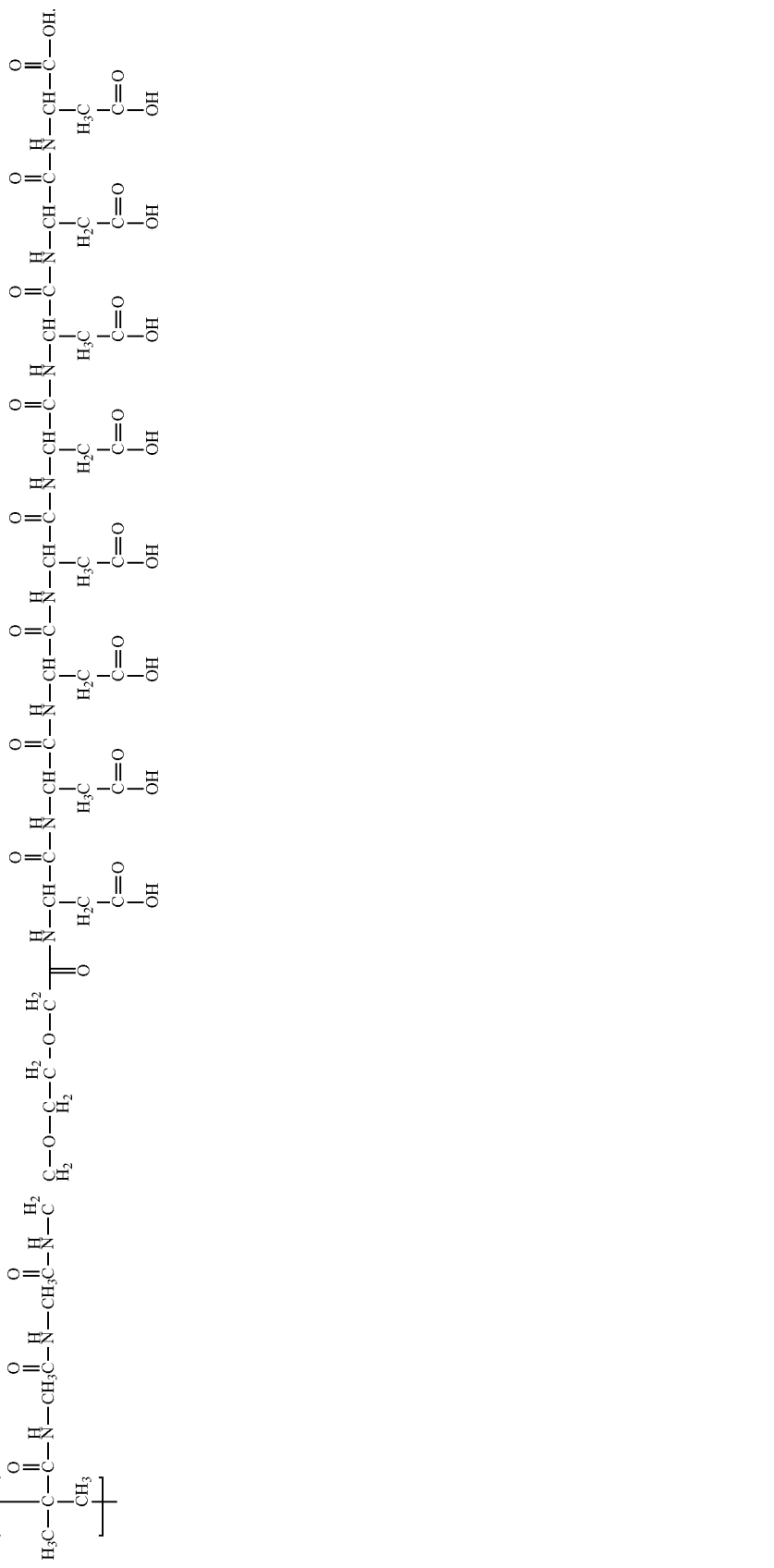

10. The method of claim 1, wherein the compound of the formula: A-B-(MA)$_n$-C-D, further comprises at least one molecule of 2-(6-hydroxy-3-oxo-3H-xanthen-9-yl)-5-(3-(3-methacrylamidopropyl)thiourei-do)benzoic acid, wherein the at least one molecule of 2-(6-hydroxy-3-oxo-3H-xanthen-9-yl)-5-(3-(3-methacrylamidopropyl)thiourei-do)benzoic acid is linked to MA.

11. The method of claim 1 wherein the compound of the formula A-B-(MA)$_n$-C-D further comprises a third group that linked to (MA)$_n$.

12. The method of claim 11, wherein the compound has the following formula:

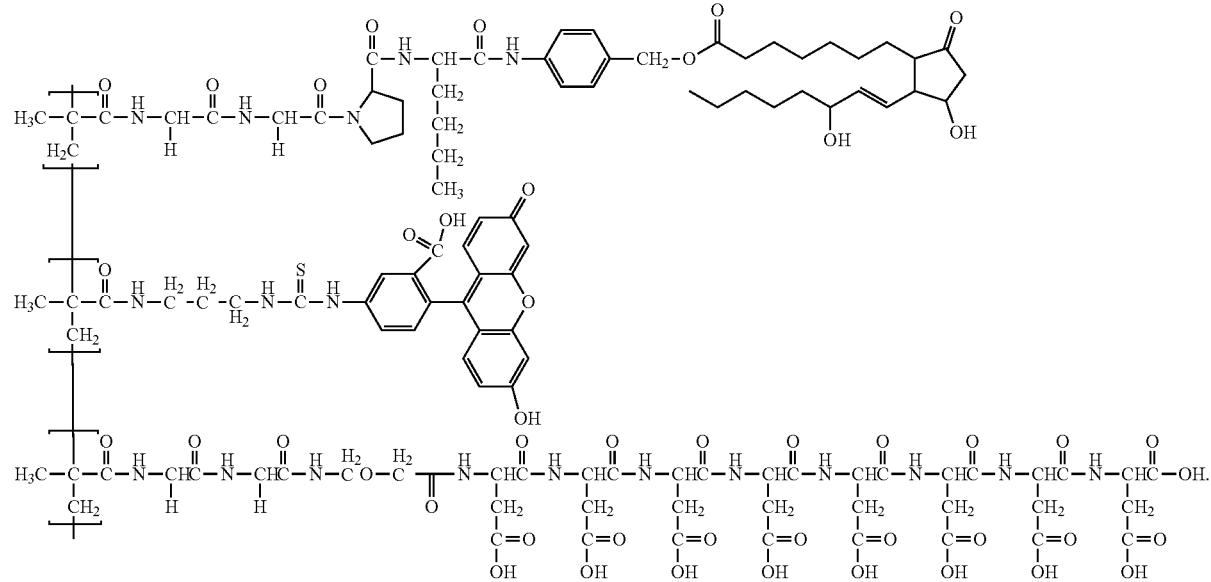

13. The method of claim 1, wherein the negatively charged oligopeptides comprise D-aspartic acid.